US010471150B2

(12) United States Patent
Konorty et al.

(10) Patent No.: US 10,471,150 B2
(45) **Date of Patent: *Nov. 12, 2019**

(54) MATERIAL AND METHOD FOR TREATING INTERNAL CAVITIES

(71) Applicant: UroGen Pharma Ltd., Raanana (IL)

(72) Inventors: Marina Konorty, Netanya (IL); Gil Hakim, Netanya (IL)

(73) Assignee: UroGen Pharma Ltd., Raanana (IL)

( * ) Notice: Subject to any disclaimer, the term of this patent is extended or adjusted under 35 U.S.C. 154(b) by 304 days.

This patent is subject to a terminal disclaimer.

(21) Appl. No.: 14/054,731

(22) Filed: Oct. 15, 2013

(65) Prior Publication Data

US 2014/0105884 A1 Apr. 17, 2014

Related U.S. Application Data

(63) Continuation-in-part of application No. 13/553,198, filed on Jul. 19, 2012, now Pat. No. 9,040,074, which is a continuation-in-part of application No. PCT/IL2011/000069, filed on Jan. 20, 2011.

(60) Provisional application No. 61/296,589, filed on Jan. 20, 2010.

(51) Int. Cl.

| | |
|---|---|
| ***A61K 47/34*** | (2017.01) |
| ***A61K 31/407*** | (2006.01) |
| ***A61K 31/704*** | (2006.01) |
| ***A61K 31/167*** | (2006.01) |
| ***A61K 31/7068*** | (2006.01) |
| ***A61K 31/397*** | (2006.01) |
| ***A61K 31/07*** | (2006.01) |
| ***A61K 31/59*** | (2006.01) |
| ***A61K 31/122*** | (2006.01) |
| ***A61K 31/337*** | (2006.01) |
| ***A61K 31/192*** | (2006.01) |
| ***A61K 38/48*** | (2006.01) |
| ***A61K 9/00*** | (2006.01) |
| ***A61K 47/10*** | (2017.01) |
| ***A61K 9/06*** | (2006.01) |
| ***A61K 47/38*** | (2006.01) |

(52) U.S. Cl.

CPC ............ *A61K 47/34* (2013.01); *A61K 9/0034* (2013.01); *A61K 9/06* (2013.01); *A61K 31/07* (2013.01); *A61K 31/122* (2013.01); *A61K 31/167* (2013.01); *A61K 31/192* (2013.01); *A61K 31/337* (2013.01); *A61K 31/397* (2013.01); *A61K 31/407* (2013.01); *A61K 31/59* (2013.01); *A61K 31/704* (2013.01); *A61K 31/7068* (2013.01); *A61K 38/4893* (2013.01); *A61K 47/10* (2013.01); *A61K 47/38* (2013.01)

(58) Field of Classification Search

None

See application file for complete search history.

(56) References Cited

U.S. PATENT DOCUMENTS

| | | | | |
|---|---|---|---|---|
| 9,950,069 | B2 | 4/2018 | Holzer et al. | |
| 10,039,832 | B2 | 8/2018 | Holzer et al. | |
| 2004/0009212 | A1 | 1/2004 | Tsai | |
| 2007/0275110 | A1 * | 11/2007 | Dott | A61K 38/4893 424/780 |
| 2009/0214685 | A1 * | 8/2009 | Hunt | A61K 9/0024 424/780 |

FOREIGN PATENT DOCUMENTS

| | | | |
|---|---|---|---|
| EP | 386960 | A2 | 9/1990 |

OTHER PUBLICATIONS

Gao et al, "Bladder tissue uptake of mitomycin C during intravesical therapy is linear with drug concentration in urine," Clin Canc Res, 4:139-143, 1998.

Schmittgen et al, "Pharmacodynamics of mitomycin C in cultured human bladder tumors," Clin Canc Res, 51:3849-3856, 1991.

International Search Report dated Jan. 18, 2012 in corresponding International Application No. PCT/IL2011/000069, 7 pages.

Written Opinion dated Jan. 18, 2012 in corresponding International Application No. PCT/IL2011/000069, 12 pages.

Wang, Hong, Advanced Pipette Holder, U.S. Pharmacopeia, http://www.pharmacopeia.cn/v29240/usp29nf24s0_m66210.html, vol. No. 29(6), p. 2020, 2007, retrieved from the internet on Jan. 23, 2018. 4 pages.

Technical Bulletin, Pluronic® Block Copolymer NF Grades (Poloxamer NF Grades), BASF The Chemical Company, 2004, 2 pages.

You et al (Intraoperative mitomycin C in dacryocystorhinostomy. Ophthal Plast Reconstr Surg. Mar. 2001;17(2):115-9), 2 pages.

* cited by examiner

*Primary Examiner* — Jake M Vu

(74) *Attorney, Agent, or Firm* — Cooley LLP

(57) ABSTRACT

Disclosed herein are materials, means and methods for sustained release of therapeutic agents for topical treatments. In particular, disclosed are means and methods for topical treatment of diseases of internal body cavities by embedding therapeutic agents in a slowly degrading biocompatible mixture applied to affected tissue.

13 Claims, 10 Drawing Sheets

MATERIAL AND METHOD FOR TREATING INTERNAL CAVITIES

REFERENCE TO RELATED APPLICATIONS

This application is a Continuation-in-Part of co-pending U.S. patent application Ser. No. 13/553,198, filed Jul. 19, 2012, which is a Continuation-in-Part of International (PCT) Patent Application No. PCT/IL2011/000069, filed Jan. 20, 2011, and claims priority from U.S. Provisional Patent Application No. 61/296,589, filed Jan. 20, 2010, each of which applications are hereby incorporated by reference in their entireties.

FIELD OF THE INVENTION

The invention relates in general to materials, means and methods for sustained release of therapeutic agents for topical treatments. It relates in particular to means and methods for topical treatment of diseases of internal body cavities by embedding therapeutic agents in a slowly degrading biocompatible mixture applied to affected tissue.

BACKGROUND OF THE INVENTION i. Topical Treatment of Diseases

The method by which a drug is delivered can have a significant effect on its efficacy. In many cases, the drug is introduced into the blood system, which then delivers it via the blood stream throughout the body. This form of access is broadly termed systemic treatment. In other cases, a more targeted delivery can focus the therapeutic effect onto the target organ, providing therapeutic benefits and avoiding side effects. Some drugs have an optimum concentration range within which maximum benefit is derived, and concentrations above or below this range can be toxic or produce no therapeutic benefit at all. In the context of the present invention, treatments that effect specific tissues or organs by directly accessing them are termed topical treatments, as opposed to systemic treatments that were described above. Sustained release of a drug involves polymers that typically release the drug at a controlled rate due to diffusion out of the polymer or by dilution of the polymer over time. Topical administration of drugs changes the rate at which drugs enter the tissue and the pharmacokinetics of the drug, thus the correctly designed materials can optimize the therapeutic effect by controlling the drug release rate. Since all internal organ tissue is water-based, administering drugs in water-based solutions is optimal.

ii. Topically Administered Drugs

Among the drugs that can be administered topically are drugs that belong to the following families:

1. Antineoplastic drugs
2. Chemotherapeutic agents
3. Anti-infective agents (e.g. Antimicrobial drugs, Antiparasitic agents, Antivirals)
4. Genito-urinary system drugs
5. Anti-inflammatory products
6. Analgesics
7. Musculoskeletal system acting drugs
8. Drugs acting on the blood and blood forming organs (Antihemorrhagics, Antithrombotic agents, antianemic drugs)
9. Dermatologic drugs (antifungals, antiseptic)
10. Gastrointestinal system (antiobesity, acid related disorders)
11. Metabolism drugs 12. Neurological drugs
13. Respiratory drugs including nasal drugs
14. Cardio-vascular drugs
15. Otological drugs
16. Anti-infective drugs
17. Corticosteroids drugs
18. Analgesics drugs
19. Antiparasitics drugs
20. Anasthetic Drugs In other cases, the topical treatment is just evolving:

21. Growth factor (e.g., for treatment of heart muscle ischemia)
22. Gene Therapy agents iii. Physical Characteristics of Internal Cavities The effectiveness of application of a topical therapeutic agent to a specific internal cavity will depend on the physical characteristics of the inner tissue of that internal cavity, in particular, characteristics such as:

Access—ease of introducing liquid or gel into the cavity

Tissue type that defines adhesiveness—ability to attach reliably and consistently polymer to the cavity tissue Internal movement—effected by gravitational motion, stretching, peristaltic motion, etc. that cause periodical changes in the shape and volume of the cavity—pressure and volume regime Wetness—to enable diffusion of drugs into the tissue Degradability mechanism—flow of liquids or aqueous solutions, e.g. urine, serous or lymphatic fluids, The specific values of cavity characteristics require careful consideration in the development of topical drugs suitable for treatment of diseases inside these cavities.

Disorders of the urothelium that result in Urinary Incontinence (UI) affect 200 million people worldwide. The United States NIH (National Institutes of Health) has estimated that as many as 25 million adult Americans have experienced or will experience transient or chronic UI. The NAFC (National Association of Continence) estimates that 75-80% of those sufferers are women, 9-13 million of whom have bothersome, severe, symptoms. It has been estimated that one in four women over the age of 18 experiences episodes of involuntary leakage of urine. One-third of men and women aged 30-70 have experienced loss of bladder control at some point in their adult lives and may be still living with the symptoms. Of men and women ages 30-70 who awaken during the night to use the bathroom, more than one-third get up twice or more per night to urinate, fitting the clinical diagnosis of nocturia. Of these adults, one in eight report they sometimes lose urine on the way to the bathroom. Overactive bladder (OAB) is especially common in older adults. It affects an estimated 1 in 11 adults in the United States. Additional common disorder of the urothelium is Interstitial Cystitis (I.C), a chronic inflammation of the bladder that causes chronic pain and discomfort effecting 4 million people in the U.S. Current available treatment options for OAB are: bladder training; pelvic floor exercises; administration of drugs such as anti-cholinergics, capsaicin, and intravesical botulinum toxin injections; and, in severe cases, bladder augmentation surgery.

The main shortcomings of orally-administered drugs in current use are their high adverse event rate resulting in patients' intolerability. Alternative routes of administration with lower adverse event rates, such as transdermal, and via suppository, have been developed. Bladder instillation of antimuscarines also has a lower adverse event rate than oral administration, but suffers from the disadvantage that it requires recurring catheterization due to the relatively short half-life of the antimuscarines, thus reducing compliance iv. Chemotherapy—Anticancer Drugs Many chemotherapy (antineoplastic) drugs used as cancer treatments bind to DNA, resulting in synthesis inhibition and strand breakage. In standard intravesical instillations, chemotherapy drugs are administered at dose concentrations of around 1 mg/ml for 1-2 hour sessions.

In the particular case of treatment of bladder cancer, the bladder tissue penetration by chemotherapy drugs—a critical parameter in treatment effectiveness—exhibits a linear relationship with the concentration of the chemotherapy drugs (see Gao X, Au J L, Badalament R A, Wientjes M G. Bladder tissue uptake of mitomycin C during intravesical therapy is linear with drug concentration in urine. Clin Cancer Res. 1998 January; 4(1):139-43)). Furthermore, chemotherapy drug penetration is 40% higher in the tumor tissue than in the adjacent normal urothelium. Gao et al demonstrated double Mitomycin C (MMC) concentration in tissue when installing 40 mg/20 ml as compared with 20 mg/20 ml MMC: human bladder tumors had a significantly higher tissue uptake of MMC than the normal bladder tissue.

The anti-tumor effect of chemotherapy drugs depends on concentration and exposure time. Schmittgen et al (see Schmittgen T D, Wientjes M G, Badalament R A, Au J L. Pharmacodynamics of mitomycin C in cultured human bladder tumors. Cancer Res. 1991 Aug. 1; 51(15):3849-56) demonstrated, both in TCC cell cultures and human bladder tumor tissue cultures, that a ten times higher concentration was needed in order to get a similar cell kill effect when exposure time to MMC was reduced from 24 hours to two hours.

The proven conclusion is that maintaining higher drug concentration for longer treatment duration will enhance the treatment efficacy.

v. Required Properties for Topical Treatment in the Bladder and Other Internal Cavities One approach to treatment of diseases of internal body cavities such as the bladder is topical application of a therapeutic agent entrained in a suitable matrix/mixture. The properties of the materials to be used in such a matrix/mixture must be adapted to the needed medical effect. Important properties include:

- Rheological properties (viscosity, thixotropy, G', G")—required for the introduction of the material into the internal cavity
- Adhesion—required to coat dependably the target tissue
- Flexibility—to comply with the volume and shape natural changes of the internal cavity under treatment
- Dilution in aqueous solution—to enable API release and natural expelling of the material through body fluids
- Mechanical properties, such as hardness, tensile strength to provide
- Duration of time that the material remains in the internal cavity before it degrades
- A suitable Active Pharmaceutical Ingredient (API)—the medical drug or drug derivative chosen from the families listed in section iii
- Loading of drug or API in the material. For certain clinical protocol the amount and concentration of the drug or API mixed into the material have to be set to a prescribed level. The amount of therapeutic agent thus used can be significantly lower than used in regular parallel instillations and more than a single API can be loaded. So the API part of the administered material may vary from zero concentration (gel only) to 50% (e.g., for DMSO).
- The ability of the matrix/mixture to release the drug in a controlled manner such that the actual drug concentration vis-à-vis the organ tissue or lining upon which the mixture is adhered will be optimal for each treatment. It is precisely the specific composition of the mixture that determines the release profile of the drug and its adsorption into the target tissue. For example, if the API is lipophilic, the addition of certain surface-active agents in given concentrations will provide for their emulsification, easier release from the drug composition and easier absorption by the internal organ lining.
- Drug viability. The material is designed and tested not to reduce the viability duration of the drug or API that is mixed into it, so that the amount that is released throughout the treatment will have the optimal therapeutic effect.

vi. Limitations of Superficial Bladder Cancer (SBC) Treatments Known in the Art

SBC is a highly-recurrent form of cancer. To lower recurrence, it is considered necessary to treat patients with a single intravesical chemotherapy instillation immediately after TUR-T.

A meta-analysis of 7 randomized trials (1,476 patients with a median follow-up of 3.4 years) has demonstrated that one chemotherapy instillation immediately after Tumor resection (TUR) decreases the relative risk of recurrence by 40% (see Sylvester R J, Oosterlinck W, van der Meijden A P. A single immediate postoperative instillation of chemotherapy decreases the risk of recurrence in patients with stage Ta T1 bladder cancer: a meta-analysis of published results of randomized clinical trials. J. Urol. 2004 June; 171(6 Pt 1):2186-90). The timing of the instillation is crucial: in all studies, instillation was administered within 24 hours. A study reported that if the first instillation was not given within 24 hours, the risk of recurrence increased twofold (see Kaasinen E, Rintala E, Hellström P, Viitanen J, Juusela H, Rajala P, Korhonen H, Liukkonen T; FinnBladder Group. Factors explaining recurrence in patients undergoing chemoimmunotherapy regimens for frequently recurring superficial bladder carcinoma. Eur Urol. 2002 August; 42(2):167-74).

Following resection and first immediate treatment patients need to be stratified by their risk for tumor progression and recurrence:

- Patients with low risk for disease progression/recurrence (30%)—need no further instillations.
- Intermediate risk patients (40-50%)—usually receive 6 additional sessions of Mitomycin C (MMC) chemotherapy instillations.
- High risk patients (20%)—are treated with 6 intravesical Bacillus Calmette-Guerin (BCG) instillations.

The efficacy of the current standard topical chemotherapy treatment for Superficial Bladder Cancer (intravesical instillation) is limited, because there is no control on the chemotherapy concentration and the time until it is expelled. In an attempt to prolong the standard treatment to two hours, some physicians dictate behavioral conditions to reduce acidity of the bladder, to reduce the volume of urine before the instillation and instill maximal concentration of chemotherapy dissolved in minimal volume of saline.

There are several obstacles and complications known that accompany the presently used methods for coating the internal wall of the bladder (and hence for topical treatments for bladder cancer):

- The mucosal membrane. One of the physiological purposes of the mucosal membrane that covers the bladder's inner wall, which is permanently soaked in urine (i.e., a watery composition), is to prevent adherence of foreign bodies to it. Therefore, any composition targeted to adhere to the internal wall of the bladder will have to overcome the difficulty of adhering to such mucosal membrane. Furthermore, since the mucosal layer is in constant contact with urine, in order to coat it, a hypothetical option would be to initially dry it. However, such an operation is not acceptable in present medical practice. Another complication stems from the membrane structure, which is composed from several cell layers where the outermost is the terminally differentiated 'umbrella' cells that are the urothelium most superficial layer. Regular biological adhesives, such that are used to stop bleeding (e.g. Tabotamp that is distributed by Johnson & Johnson, NJ, USA), can bond strongly through the wet surface and peel-off that delicate, outermost layer and thus damage the membrane. The achievement of a satisfactory non-damaging coating of wet, non-adherent mucosal tissue is very challenging indeed.

The bladder's natural expansion and collapse. The bladder is essentially muscular tissue and its wall is naturally highly flexible. The inner volume of a mature bladder varies greatly, from a collapsed or 'empty' state with a volume of 0-30 ml up to a filled bladder with a volume of up to 500-600 ml (though the bladder usually fills only up to 150-200 ml before micturition point, that is, when the individual feels the urge to urinate and indeed vacates the bladder. Therefore, providing a composition that has the capacity to adhere and conform to the bladder wall without damaging the outer layer, adapt itself to the bladder's morphology in spite of the great variance in volume and the fact that it is permanently changing its form and volume and stay adhered to it is considered an enormous challenge.

Further to the above mentioned difficulties to adhere onto a mucosal membrane, it is also highly challenging to do so while avoiding the peeling-off of the outermost layer of the membrane—due to adhering shear forces or adhesion between tissue areas. So while biological glues that can stop bleeding can also adhere through the wet mucosal layer, their rigidity compromises the integrity of the outermost layer and negates the required therapeutic effect.

The same obstacles, to even greater extent, are relevant to the treatment of the same cancer (transitional cell carcinoma) in the upper urinary tract. TCC in the upper urinary tract is a rare urological disease and has a propensity for multifocality, local recurrence, and development of metastases. Almost 5% of all urothelial neoplasms occur in the kidney and ureters. The standard treatment for patients with upper tract TCC and a normal kidney is a complete removal of the involved kidney, ureter and bladder cuff. A less-invasive treatment, namely resection of tumors followed by instillation with chemotherapy or immunotherapy, is recommended for patients with anatomic or functional solitary kidneys, bilateral upper-tract TCC, base line renal insufficiency, or inability to tolerate major surgery. Patients with a normal contralateral kidney who have small, low-grade lesions can also be reasonable candidates for this organ conserving management.

Topical immunotherapy or chemotherapy instillations for treatment of UTUC are used as primary or adjuvant treatment in order to reduce tumor recurrence. Topical instillation is performed using either infusion through a percutaneous nephrostomy tube, via a retrograde ureteral catheter, or by retrograde reflux from the bladder with an indwelling double-J stent. The main disadvantage in all these treatments is the short residual duration of the active agent in the treated area resulting in a low exposure time essential for treatment efficacy. This may be one of the reasons for the shorter average disease-free duration of upper tract TCC patients, compared to lower tract TCC patients.

Another bladder disease is overactive bladder (OAB)—when the bladder contracts suddenly without patient's control when the bladder is not full. This syndrome affects an estimated 1 in 11 adults in the United States—especially common in older adults.

Current available treatment options for OAB are: bladder training, pelvic floor exercises, drug therapy such as anti-cholinergics, capsaicin, intravesical botulinum toxin injections and in severe cases—bladder augmentation surgery.

Current oral drugs have high adverse event rate which leads to patients' intolerability. Bladder instillation with antimuscarines has been tried with lower adverse event rate, but require recurrent catheterization due to the drug relatively short half-life that reduces compliance.

Despite promising results the drawbacks to intravesical botulinum toxin injections are numerous: the cystoscopic injection requires proficiency and authorization of the physician, some degree of anesthetic administration is required, the botulinum toxin effects only the injected anatomical locations and the treatment may lead to temporary urinary retention and need for self-catheterization.

vii. Mechanical Support and Sustained Drug Release in Minimally-Invasive Surgery The limited number of access ports used in laparoscopic surgery may impair the ability of the surgeon to achieve adequate retraction and exposure, or to stabilize "moving targets" while operating on nonfixed organs. Current solutions include adding more ports or using a hand-assisted technique—which have the disadvantages of being more invasive, possibly creating a cumbersome situation of multiple instruments in a limited working space—or the use of temporary sutures that pass through the abdominal wall.

The current invention provides means by which the organs can be held mechanically in place by injecting the invented materials into the cavity and letting them to solidify and support the internal organs. This invented materials and method have the additional advantages of a) serving as a soothing dressing for the surgery cuts, b) contribution to healing through sustained release of anti-infection drug and analgesic drug for a therapeutically-significant duration (e.g., over 6 hours), and c) avoiding the need for further surgical or medical procedure, by natural degradation of the material and its expelling from the body.

Similar method, but with a different family of materials can be used to prevent the adhesion of tissues between organs in the treated area, which may often occur during laparoscopic surgery.

viii. Current State-of-the-Art

To the best of the inventors' knowledge, a method for treating diseases of the bladder or other inner cavities based on production of a solidified coating layer and affixing it onto the internal wall of the bladder or other cavities, followed by continuous release of the therapeutic agent(s) from the coating, remains unknown in the art.

Furthermore, the application of the substrate material such that it creates a continuous layer substantially affixed to the mucosal lining of the bladder or the outermost tissue of other internal cavity for prolonging the exposure of the drug to the targeted cells is neither trivial nor obvious to any person skilled in the art.

Compositions known in the prior art as sustained-release substrates for the treatment of bladder cancer (for example, the invention disclosed in U.S. Pat. Appl. US2006/0127420 to Chung) are lipophilic (oil-based). Given that the inner bladder wall is mucosal, essentially and permanently soaked in an aqueous medium (i.e., urine), a drug embedded in a hydrophilic medium would more effectively diffuse through the matrix/mixture and conveniently reach the bladder wall, allowing in that way an intimate, continuous contact between the drug and the bladder wall.

Thus, there remains a long-felt and unmet need for a material with the following properties: it is hydrophilic; it provides a homogeneous layer that can securely adhere to the surfaces of internal body cavities, in particular, mucosal tissue of such cavities as the bladder; it remains attached despite the natural motions of the tissue to which it is attached; it is easily applied; it is biocompatible; it provides a continuous sustained release of a therapeutic agent; the rate of release of the therapeutic agent is determined by the concentration of the agent and the rate of degradation of the material; and after the material degrades, it is excreted from the body by the body's own natural processes.

SUMMARY OF THE INVENTION

The compositions disclosed herein, and the use thereof in treatments of bladder disorders and urothelium dysfunction, are designed to meet this long-felt need. In particular, mucoadhesive, bioerodible, biocompatible thermoreversible hydrogel compositions comprising a therapeutically active agent are disclosed that after insertion into a body cavity, solidify and form a drug reservoir inside the cavity. The compositions and means for delivering them produce complete contact with and coverage of the bladder wall, thereby providing drug delivery to the entire bladder, in contrast to delivery induced by local injections. They additionally produce a high topical drug concentration in the cavity walls but low systemic exposure. By these means the invention herein disclosed provides increased bioavailability, enhanced efficacy and reduced toxicity.

It comprises a series of systems that combine therapeutic materials and application means for the topical treatment of diseases that are focused in internal cavities, such as a system for treating Superficial Bladder Cancer (SBC).

It is therefore an object of the present invention to disclose the use of a thermoreversible hydrogel composition in a system for delivery of a therapeutic agent to the urinary tract, characterized in that said thermoreversible hydrogel composition comprises a thermoreversible hydrogel It is a further object of this invention to disclose such a use of a thermoreversible hydrogel composition in a system for delivery of a therapeutic agent to the urinary tract, wherein said composition additionally comprises an effective amount of at least one therapeutic agent for treatment of the urinary tract.

It is a further object of this invention to disclose such a use of a thermoreversible hydrogel composition in a system for delivery of a therapeutic agent to a mucosal or serous membrane, wherein said composition additionally comprises an effective amount of a therapeutic agent for treatment of a mucosal or serous membrane.

It is a further object of this invention to disclose such a use of a thermoreversible hydrogel composition in a system for delivery of a therapeutic agent to a mucosal or serous membrane, wherein said mucosal or serous membrane is located at an internal cavity chosen from the group consisting of, mouth, nasal sinus, paranasal sinus, gallbladder, esophagus, rectum, lungs, vagina, uterus, stomach, renal pelvis, pleura, abdomen, peritoneum, pelvis, liver, kidney, heart, intestine, brain, and vertebral column.

In some embodiments of the invention, said thermoreversible hydrogel comprises between 20% and 30% (w/w) ethylene oxide/propylene oxide block copolymer; between 0.05% and 0.5% (w/w) hydroxypropylmethylcellulose (HPMC); between 0.1% and 2.5% (w/w) polyethylene glycol (PEG)-400; and the balance water.

In some embodiments of the invention, said thermoreversible hydrogel comprises between 20% and 30% (w/w) ethylene oxide/propylene oxide block copolymer; between 0.1% and 0.3% (w/w) HPMC; between 0.1% and 1.8% (w/w) PEG-400; and the balance water.

In some embodiments of the invention, said thermoreversible hydrogel comprises between 18% and 40% (w/w) ethylene oxide/propylene oxide block copolymer; between 0.05% and 0.8% (w/w) CMC; between 0.1% and 2.5% (w/w) PEG-400; and the balance water.

In some embodiments of the invention, said thermoreversible hydrogel comprises between 12-30% Pluronic F127; between 5-30% Pluronic F68; between 0.05% and 2% (w/w) CMC; between 0.1% and 2.5% (w/w) PEG-400; and the balance water.

It is a further object of this invention to disclose such a use as defined in any of the above, wherein said thermoreversible hydrogel additionally comprises at least one component selected from the group consisting of adhesive and thickening compounds; bonding agents; pH-modifying substances; diffusion coatings; plasticizers; components for increasing permeability within the formulation; swellable excipients; matrix forming polymers; tight junction modifiers/cell membrane permeability enhancers; and any combination thereof.

In some embodiments of the invention, said bonding agent is selected from the group consisting of polycarbophil, cellulose, microcrystalline cellulose, cellulose derivatives, HPMC, hydroxypropylcellulose (HPC), low-substituted hydroxypropylcellulose, dicalcium phosphate, lactose, sucrose, ethylcellulose, hydroxypropymethylcellulose acetate succinate (HPMCAS), polyvinylpyrrolidone (PVP), vinylpyrrolidone/vinyl acetate copolymer, polyethylene glycol, polyethylene oxide, polymethacrylates, polyvinyl alcohols (PVA), partially hydrolysed polyvinyl acetate (PVAc), polysaccharides, hyaluronic acid, fats, fatty acid derivatives, and any combination thereof.

In some embodiments of the invention, said diffusion coating is chosen from the group consisting of ethylcelluloses and polymethacrylates, cellulose acetate and cellulose acetate butyrate or any combination thereof.

In some embodiments of the invention, said component for increasing permeability within the formulation is chosen from the group consisting of polyethylene glycols, PVP, PVA, HPMC, HPC, hydroxyethylcelluloses (HEC), methylcellulose (MC), carboxymethylcelluloses and their salts, dextrins, maltodextrins, cylcodextrins, dextrans, urea, salts, sugars, sugar alcohols, and any combination thereof.

In some embodiments of the invention, said swellable excipient is selected from the group consisting of polyvinylpyrrolidones, crospovidones, crosslinked sodium carboxymethylcellulose, crosslinked sodium carboxymethylstarch, polyethylene oxides, polymethyacrylates, L-HPC, cellulose acetate, ethylcellulose, polymethacrylates, high-molecular weight polyethylene oxides, xanthan gum, copolymers of vinylpyrrolidone and vinyl acetate, polyvinylpyrrolidones, crospovidones, crosslinked sodium carboxymethylcellulose, crosslinked sodium carboxymethylstarch, poly(hydroxyalkyl methacrylate), alginates, galactomannans, and any combination thereof.

In some embodiments of the invention, said matrix forming polymer is selected from the group consisting of hydroxyethylmethylcelluloses, HPC, HEC, MC, ethylcelluloses, alkylcelluloses, hydroxyalkylcelluloses, hydroxyalkylmethylcelluloses, sodium CMCs, alginates, galactomannans, xanthans, polyethylene oxides, polyacrylic acids, polymethacrylic acids, polymethacrylic acid derivatives, polyvinyl alcohols, partially hydrolysed polyvinyl acetate, polyvinylpyrrolidone, agar, pectin, gum arabic, tragacanth, gelatin, starch, starch derivatives poly(propylene oxide) (PPO), poly(lactide-co-glycolic acid) (PLGA), poly(N-isopropylacrylamide) (PNIPAM), poly(propylene fumarate) (PPF), polyurethane (PU), poly(organophosphazene) (POP), stearic acid, poly(acrylic acid), glyceryl stearate, cetearyl alcohol, sodium stearoyl lactylate, hydroxy-lanolin, and any combination thereof.

It is a further object of this invention to disclose such a use as defined in any of the above, further characterized in that said composition releases said therapeutic agent, over a temperature range of 36° C.-42° C. and a pH range of between 5.5 and 8.0, at a rate of 80% in a time range of between 3 and 30 hours.

It is a further object of this invention to disclose such a use as defined in any of the above, further characterized in that said composition releases said therapeutic agent, over a temperature range of 36° C.-42° C. and a pH range of between 1 and 9.0, at a rate of 80% in a time range of between 3 and 30 hours.

It is a further object of this invention to disclose such a use as defined in any of the above, wherein said therapeutic agent for treatment of the urinary tract is selected from the group consisting of antineoplastic agents, chemotherapeutic agents, anti-infective agents, antimicrobial agents, antiparasitic agents, antiviral agents, agents acting on the blood, antihemorrhagics, antithrombotic agents, antifungals, antiseptics, agents for treating diseases of the genito-urinary system, anti-inflammatory agents, neurological agents, gene therapy agents, corticosteroids, analgesic and anesthetic agents, growth factors, VEGF, inhibitory factors, LIF, proteins, mucin, and any combination thereof.

It is a further object of this invention to disclose such a use as defined in any of the above, wherein said therapeutic agent for treatment of the urinary tract is selected from the group consisting of Mitomycin C, Deoxrubicin, Valrubicin, and Gemcitabine, Thiotepa, Ethoglucid (Epodyl), Epirubicin, Pirarubicin, Apaziquone, Vicinium, botulinium toxin, and interleukin-2.

It is a further object of this invention to disclose a use as defined in any of the above, wherein said pharmaceutically active agent is botulinum toxin. In some embodiments of the invention, said pharmaceutically active agent is selected from the group consisting of otulinum toxin A, botulinum toxin B, botulinum toxin $C_1$, botulinum toxin D, botulinum toxin E, botulinum toxin F and botulinum toxin G. In some embodiments of the invention, said pharmaceutically active agent is selected from the group consisting of anticholinergic agents, and antimuscarinic agents, beta-3 agonists, pentosan polysulfate, amitriptyline, heparin-binding epidermal growth factor (HB-EGF), all-trans-retinoic acid (ATRA), derivatives of antiproliferative factor (APF), cannabinoid-2 receptor blockers, memantine, N-methyl-D-aspartate (NMDA)-receptor blockers, Parthenolide, inhibitors of NF-κB, calcium glycerophosphate, Metamucil, and Chondroitin sulfate It is a further object of this invention to disclose a use as defined in any of the above, wherein said composition is for treatment of a bladder disorder characterized by bladder spasms. In some embodiments of the invention, said disorder is selected from the group consisting of urinary incontinence due to unstable bladder or unstable detrusor sphincter; voiding complications due to detrusor overactivity or a hypertrophied bladder neck; neurogenic bladder dysfunction secondary to conditions such as Parkinson's disease, spinal cord injury, stroke or multiple sclerosis; and bladder pathologies characterized by a spasm reflex, overactive bladder, interstitial cystitis, stress incontinence, urge incontinence, or neurogenic bladder.

It is a further object of this invention to disclose a use as defined in any of the above, wherein said composition comprises 0.2-20 U/kg body weight of botulinum toxin.

It is a further object of this invention to disclose a use as defined in any of the above, wherein said biocompatible mucoadhesive thermoreversible hydrogel is characterized by an instillation temperature of between 20° C. and 42° C.

It is a further object of this invention to disclose a use as defined in any of the above, wherein said biocompatible mucoadhesive thermoreversible hydrogel is characterized by an instillation temperature of between 4° C. and 60° C.

It is a further object of this invention to disclose a use as defined in any of the above, wherein said biocompatible mucoadhesive thermoreversible hydrogel is characterized by a gel point below 33° C.

It is a further object of this invention to disclose such a use as defined in any of the above, wherein said system is further characterized in that it is designed to release said therapeutic agent continuously for at least 12 hours.

It is a further object of this invention to disclose a method for administering a therapeutic agent to the internal surface of an internal body cavity, comprising:

incorporating an effective amount of said therapeutic agent into a biocompatible sustained-release material chosen from the group consisting of (a) biocompatible sustained-release materials comprising between 20% and 30% (w/w) ethylene oxide/propylene oxide block copolymer, between 0.05% and 0.5% (w/w) HPMC, between 0.1% and 2.5% (w/w) PEG-400, and the balance water; and (b) biocompatible sustained-release materials comprising between 20% and 30% (w/w) ethylene oxide/propylene oxide block copolymer; between 0.1% and 0.3% (w/w) HPMC; between 0.1% and 1.8% (w/w) PEG-400; and the balance water;

inflating a balloon to open said internal body cavity to a substantially symmetrical shape;

introducing said biocompatible sustained-release material into said internal body cavity;

applying said biocompatible sustained-release material to at least part of the internal surface of said internal body cavity;

applying force to said material, thereby spreading it over at least part of the internal surface of said internal cavity;

causing said biocompatible sustained-release material to adhere to said internal surface of said internal body cavity; and, releasing said therapeutic agent into said internal body cavity under conditions chosen from the group consisting of:

a temperature of 36-42° C.; pH in the range of 5.5-8.0, and at a rate of 80% in a time range of 3 to 30 hours;

a temperature of 36-42° C.; pH in the range of 1-9.0, and at a rate of 80% in a time range of 3 to 30 hours; and, It is a further object of this invention to disclose such a method, additionally comprising a step of providing said material with at least one component selected from the group consisting of adhesive and thickening compounds; at least one substance selected from the group consisting of polycarbophil, cellulose, microcrystalline cellulose, cellulose derivatives, dicalcium phosphate, lactose, PVP and sucrose, ethylcellulose, hydroxypropymethylcellulose acetate succinate (HPMCAS), PVP, vinylpyrrolidone/vinyl acetate copolymer, polyethylene glycol, polyethylene oxide, polymethacrylates, polyvinyl alcohols (PVA), partially hydrolysed polyvinyl acetate (PVAc), polysaccharides, fats and fatty acid derivatives and any combination thereof; pH-modifying substances; at least one substance selected from the group consisting of ethylcelluloses and polymethacrylates, cellulose acetate, cellulose acetate butyrate and any combination thereof; plasticizers; at least one substance selected from the group consisting of polyvinylpyrrolidones, crospovidones, crosslinked sodium carboxymethylcellulose, crosslinked sodium carboxymethylstarch, polyethylene oxides, polymethyacrylates, low-substituted hydroxypropylmethylcellulose (L-HPC), cellulose acetate, ethylcellulose and polymethacrylates, high-molecular weight polyethylene oxides, xanthan gum, copolymers of vinylpyrrolidone and vinyl acetate, polyvinylpyrrolidones, crospovidones, crosslinked sodium carboxymethylcellulose, crosslinked sodium carboxymethylstarch, poly(hydroxyalkyl methacrylate), alginates, galactomannans, and any combination thereof; at least one substance chosen from the group consisting of polyethylene glycols, PVP, PVA, HPC, hydroxyethylcelluloses (HEC), MC, carboxymethylcelluloses or their salts, dextrins, maltodextrins, cylcodextrins, dextrans urea, salts, sodium chloride, potassium chloride, ammonium chloride, sugars, sucrose, lactose, glucose, fructose, maltose, sugar alcohols, mannitol, sorbitol, xylitol, lactitol, and any combination thereof; at least one substance chosen from the group consisting of hydroxyethylmethylcelluloses, hydroxypropylcelluloses (HPC), hydroxyethylcelluloses methylcelluloses (MC), ethylcelluloses, alkylcelluloses, hydroxyalkylcelluloses hydroxyalkylmethylcelluloses, sodium carboxymethylcelluloses (NaCMC), alginates, galactomannans, xanthans, polyethylene oxides, polyacrylic acids, polymethacrylic acids, polymethacrylic acid derivatives, polyvinyl alcohols (PVA), partially hydrolysed polyvinyl acetate (PVAc), polyvinylpyrrolidone (PVP), agar, pectin, gum arabic, tragacanth, gelatin, starch, starch derivatives and any combination thereof; and any combination thereof.

It is a further object of this invention to disclose such a method, wherein said step of releasing said therapeutic material into said internal body cavity further comprises a step of dissolving said biocompatible sustained-release material in body fluid found within said internal body cavity, whereby said therapeutic agent is released from said biocompatible sustained-release material.

It is a further object of this invention to disclose such a method, wherein said step of applying force to said material further comprises a step of filling said catheter balloon with a liquid and positioning the patient to utilize the gravitational forces directly toward the target tissue during the solidification of the material and cause optimal adhesion to that target tissue.

It is a further object of this invention to disclose such a method, wherein said step of applying force to said material further comprises a step of changing the position of the patient before applying partial doses of material to enable substantially full coating of the whole targeted internal cavity surface.

It is a further object of this invention to disclose such a method, wherein said step of applying force to said material further comprises inserting a magnetic material chosen from the group consisting of a magnet, a magnetic metal, and a ferromagnetic liquid into said balloon; and applying an external magnetic field such that the interaction said magnetic material and said external magnetic field causes said magnetic material to move within said balloon, thereby applying force to at least part of the internal surface of said internal cavity.

It is therefore an object of the present invention to disclose a hydrophilic biocompatible sustained-release material comprising Pluronic F-127 and Hydroxypropylmethylcellulose (HPMC) in amounts effective to produce a hydrogel composition of sufficiently low viscosity at room temperature to be injectable into an internal body cavity via a tube inserted within a urinary catheter, trocar or the working channel of an endoscope.

It is a further object of this invention to disclose such a material, further comprising PEG-400 or PEG-800.

It is a further object of this invention to disclose such a material as defined in any of the above, additionally comprising at least one active ingredient (API).

It is a further object of this invention to disclose such a material as defined in any of the above, wherein said API comprises excipients selected from acids or buffer substances adapted to modify the pH so as to reduce the dependence of said release of active ingredient on the pH of the release medium.

It is a further object of this invention to disclose such a material as defined in any of the above, additionally comprising at least one more compounds selected from adhesive and thickening compounds; bonding agents; pH-modifying substances; diffusion coating; plasticizers; matrix permeability increasing components; swellable excipients matrix-forming polymers; diffusion-controlled or pulsatile formulations; reverse thermal gelaton agents or any combination thereof.

It is a further object of this invention to disclose such a material as defined in any of the above, wherein said adhesive and thickening compounds are selected from a group consisting of polycarbophil, acrylic acid crosslinked, divinyl glycol, hydroxypropylmethylcellulose (HPMC), polyvinylpyrrolidone (PVP), methylcellulose (MC), hydroxy-propylcellulose (HPC), other hydroxyalkylcelluloses, hydroxyalkylmethylcelluloses, carboxy-methylcelluloses and salts thereof, polyacrylic acids, polymethacrylates, gelatin, starch or starch derivatives, as well as gums like guar gum and xanthan gum or any combination thereof.

It is a further object of this invention to disclose such a material as defined in any of the above, wherein said bonding agents are selected from a group consisting of polycarbophil, cellulose, microcrystalline cellulose, cellulose derivatives such as, for example, HMPC, HPC and low-substituted hydroxypropylcellulose (L-HPC), dicalcium phosphate, lactose, PVP and sucrose, ethylcellulose, hydroxypropymethylcellulose acetate succinate (HPMCAS), PVP, vinylpyrrolidone/vinyl acetate copolymer, polyethylene glycol, polyethylene oxide, polymethacrylates, polyvinyl alcohols (PVA), partially hydrolysed polyvinyl acetate (PVAc), polysaccharides (e.g. alginic acid, alginates, galactomannans) waxes, fats and fatty acid derivatives or any combination thereof.

It is a further object of this invention to disclose such a material as defined in any of the above, wherein said pH-modifying substances are selected from a group consisting of acids, bases and buffer, adipic acid, malic acid, L-arginine, ascorbic acid, aspartic acid, benzenesulphonic acid, benzoic acid, succinic acid, citric acid, ethanesulphonic acid, 2-hydroxyethanesulphonic acid, fumaric acid, gluconic acid, glucuronic acid, glutamic acid, potassium hydrogen tartrate, maleic acid, malonic acid, methanesulphonic acid, toluenesulphonic acid, trometamol, tartaric acid. Citric acid, succinic acid, tartaric acid, potassium hydrogen tartrate are preferably employed or any combination thereof.

It is a further object of this invention to disclose such a material as defined in any of the above, wherein said diffusion coating are selected from a group consisting of ethylcelluloses and polymethacrylates such as, for example, EUDRAGIT® NE, EUDRAGIT® RS and RL, cellulose acetate and cellulose acetate butyrate or any combination thereof.

It is a further object of this invention to disclose such a material as defined in any of the above, wherein the proportion of the plasticizer is from 0 to 50%, preferably 0 to 35% of the hydrogel composition.

It is a further object of this invention to disclose such a material as defined in any of the above, wherein said water-soluble polymers are selected from a group consisting of polymerspolyethylene glycols, PVP, PVA, HPMC, HPC, hydroxyethylcelluloses (HEC), MC, carboxymethylcelluloses or their salts, dextrins, maltodextrins, cylcodextrins, dextrans urea, salts, sodium chloride, potassium chloride, ammonium chloride, sugars, sucrose, lactose, glucose, fructose, maltose, sugar alcohols, mannitol, sorbitol, xylitol, lactitol, or any combination thereof.

It is a further object of this invention to disclose such a material as defined in any of the above, wherein said swellable excipients are selected from a group consisting of polyvinylpyrrolidones, crospovidones, crosslinked sodium carboxymethylcellulose, crosslinked sodium carboxymethylstarch, polyethylene oxides, polymethyacrylates, low-substituted hydroxypropylmethylcellulose (L-HPC), cellulose acetate, ethylcellulose and polymethacrylates, high-molecular weight polyethylene oxides, xanthan gum, copolymers of vinylpyrrolidone and vinyl acetate, polyvinylpyrrolidones, crospovidones, crosslinked sodium carboxymethylcellulose, crosslinked sodium carboxymethylstarch, poly(hydroxyalkyl methacrylate), alginates and galactomannans and mixtures thereof or any combination thereof.

It is a further object of this invention to disclose such a material as defined in any of the above, wherein said reverse thermal gelaton compositions are selected from a group consisting of Poloxamers, Poloxamer 407 or any combination thereof.

It is a further object of this invention to disclose such a material as defined in any of the above, wherein said water-swellable matrix-forming polymers compositions are selected from a group consisting ohydroxy-propylmethylcelluloses (HPMC), hydroxyethylmethylcelluloses, hydroxypropylcelluloses (HPC), hydroxyethylcelluloses methylcelluloses (MC), ethylcelluloses, alkylcelluloses, hydroxy-alkylcelluloses hydroxyalkylmethylcelluloses, sodium carboxymethylcelluloses (NaCMC), alginates, galactomannans such as, for example, guar and carob flour, xanthans, polyethylene oxides, polyacrylic acids, polymethacrylic acids, polymethacrylic acid derivatives, polyvinyl alcohols (PVA), partially hydrolysed polyvinyl acetate (PVAc), polyvinylpyrrolidone (PVP), agar, pectin, gum arabic, tragacanth, gelatin, starch or starch derivatives or any combination thereof.

It is a further object of this invention to disclose such a material as defined in any of the above, wherein said material is formulated as a homogeneous mixture.

It is a further object of this invention to disclose such a material as defined in any of the above, wherein said material is administered orally, topically, intranasal, vaginally, rectal, ocular and parenteral routes.

It is a further object of this invention to disclose such a material, wherein the solubility of said material is sufficiently high that said material will completely degrade in less than 24 hours after incorporation into an internal body cavity.

It is a further object of this invention to disclose such a material, wherein the solubility of said material is sufficiently high that said material will completely degrade in less than 16 hours after incorporation into an internal body cavity.

It is a further object of this invention to disclose such a material as defined in any of the above, wherein the instillation temperature of said material is between 20° C. and 42° C.

It is a further object of this invention to disclose such a material, wherein said material is characterized by a gel point below 20° C.

It is a further object of this invention to disclose such a material as defined in any of the above, adapted to adhere to the surface of mucosal tissue.

It is a further object of this invention to disclose such a material as defined in any of the above, further comprising an effective amount of a therapeutic agent.

It is a further object of this invention to disclose such a material, comprising 20-30% Pluronic F-127; 0-1.8% PEG-400; 0.1%-0.3% HPMC; an effective amount of a therapeutic agent; and the balance water.

It is a further object of this invention to disclose such a material, comprising 20-30% Pluronic F-127; 0-2.5% PEG-400; 0.05%-0.5% HPMC; an effective amount of a therapeutic agent; and the balance water.

It is a further object of this invention to disclose such a material, wherein said therapeutic agent is chosen from the group consisting of Mitomycin C, Deoxrubicin (with or without antibiotics), Valrubicin, and Gemcitabine, Thiotepa, Ethoglucid (Epodyl), Epirubicin, Pirarubicin, Apaziquone, Botulinium Toxin and Vicinium.

It is a further object of this invention to disclose such a material, wherein said therapeutic agent is mitomycin C.

It is a further object of this invention to disclose such a material, wherein said mitomycin C is present in a concentration of 0.05%-0.2%.

It is a further object of this invention to disclose such a material, wherein said mitomycin C is present in a concentration of 0.025%-0.3%.

It is a further object of this invention to disclose such a material as defined in any of the above, wherein the solubility of said material is sufficiently low that said therapeutic agent is continuously released for at least 12 hours.

It is a further object of this invention to disclose such a material as defined in any of the above, wherein the solubility of said material is sufficiently low that said therapeutic agent is continuously released for at least 2 hours.

It is a further object of this invention to disclose such a material as defined in any of the above, wherein the solubility of said material is sufficiently low that said therapeutic agent is continuously released for at least 16 hours.

It is a further object of this invention to disclose such a material as defined in any of the above, wherein the solubility of said material is sufficiently low that said therapeutic agent is continuously released for at least 18 hours.

It is a further object of this invention to disclose the use of the material as defined in any of the above in a sustained-release topical treatment of a condition affecting an internal body cavity.

It is a further object of this invention to disclose the use of the material as defined in any of the above in a sustained-release topical treatment for at least one selected from a group of internal cavities that includes, among others, the urinary bladder, mouth, nasal and paranasal sinus, gallbladder, esophagus, rectum, lungs, vagina, uterus, stomach, renal pelvis, pleura, abdomen, peritoneum, pelvis, liver, kidney, heart, intestine, brain, vertebral column, etc.

It is a further object of this invention to disclose a material as defined in any of the above, additionally comprising at least one active ingredient (API).

It is a further object of this invention to disclose a material, wherein said therapeutic agent is Botulinium Toxin, that intended for treating a bladder disorder wherein said bladder disorder is characterized by bladder spasms.

In some embodiments, said disorder is selected from the group consisting of urinary incontinence due to unstable bladder or unstable detrusor sphincter; voiding complications due to detrusor overactivity or a hypertrophied bladder neck; neurogenic bladder dysfunction secondary to conditions such as Parkinson's disease, spinal cord injury, stroke or multiple sclerosis; and bladder pathologies characterized by a spasm reflex, overactive bladder, interstitial cystitis, stress incontinence, urge incontinence, or neurogenic bladder.

In some embodiments, said step of applying to a bladder cavity a biocompatible mucoadhesive thermoreversible hydrogel into which a pharmaceutically active agent for treating said bladder disorder has been incorporated comprises applying to a bladder cavity a biocompatible mucoadhesive thermoreversible hydrogel comprising 0.2-20 U/kg body weight of botulinum toxin.

It is a further object of this invention to disclose such a material as defined in any of the above, wherein said material comprises excipients selected from acids or buffer substances adapted to modify the pH so as to reduce the dependence of said release of active ingredient on the pH of the release medium.

It is a further object of this invention to disclose such a material as defined in any of the above, additionally comprising at least one more compounds selected from adhesive and thickening compounds; bonding agents; pH-modifying substances; diffusion coating; plasticizers; matrix permeability increasing components; swellable excipients matrix-forming polymers; diffusion-controlled or pulsatile formulations; reverse thermal gelaton agents or any combination thereof.

It is a further object of this invention to disclose such a material as defined in any of the above, wherein said adhesive and thickening compounds are selected from a group consisting of polycarbophil, acrylic acid crosslinked, divinyl glycol, hydroxypropylmethylcellulose (HPMC), polyvinylpyrrolidone (PVP), methylcellulose (MC), hydroxy-propylcellulose (HPC), other hydroxyalkylcelluloses, hydroxyalkylmethylcelluloses, carboxy-methylcelluloses and salts thereof, polyacrylic acids, polymethacrylates, gelatin, starch or starch derivatives, as well as gums like guar gum and xanthan gum or any combination thereof.

It is a further object of this invention to disclose such a material as defined in any of the above, wherein said bonding agents are selected from a group consisting of polycarbophil, cellulose, microcrystalline cellulose, cellulose derivatives such as, for example, HMPC, HPC and low-substituted hydroxypropylcellulose (L-HPC), dicalcium phosphate, lactose, PVP and sucrose, ethylcellulose, hydroxypropymethylcellulose acetate succinate (HPMCAS), PVP, vinylpyrrolidone/vinyl acetate copolymer, polyethylene glycol, polyethylene oxide, polymethacrylates, polyvinyl alcohols (PVA), partially hydrolysed polyvinyl acetate (PVAc), polysaccharides (e.g. alginic acid, alginates, galactomannans) waxes, fats and fatty acid derivatives or any combination thereof.

It is a further object of this invention to disclose such a material as defined in any of the above, wherein said pH-modifying substances are selected from a group consisting of acids, bases and buffer, adipic acid, malic acid, L-arginine, ascorbic acid, aspartic acid, benzenesulphonic acid, benzoic acid, succinic acid, citric acid, ethanesulphonic acid, 2-hydroxyethanesulphonic acid, fumaric acid, gluconic acid, glucuronic acid, glutamic acid, potassium hydrogen tartrate, maleic acid, malonic acid, methanesulphonic acid, toluenesulphonic acid, trometamol, tartaric acid. Citric acid, succinic acid, tartaric acid, potassium hydrogen tartrate are preferably employed or any combination thereof.

It is a further object of this invention to disclose such a material as defined in any of the above, wherein said diffusion coating are selected from a group consisting of ethylcelluloses and polymethacrylates such as, for example, EUDRAGIT® NE, EUDRAGIT® RS and RL, cellulose acetate and cellulose acetate butyrate or any combination thereof.

It is a further object of this invention to disclose such a material as defined in any of the above, wherein said plasticizers are selected from a group consisting of citric acid derivatives, triethyl citrate, tributyl citrate, acetyl triethyl citrate, phthalic acid derivatives, dimethyl phthalate, diethyl phthalate, dibutyl phthalate, benzoic acid and benzoic esters, other aromatic carboxylic esters, trimellithic esters, aliphatic dicarboxylic esters, dialkyl adipates, sebacic esters, in particular diethyl sebacate, tartaric esters, glycerol monoacetate, glycerol diacetate or glycerol triacetate, polyols, glycerol, 1,2-propanediol, polyethylene glycol of varying chain length, fatty acids and derivatives, glycerol monostearates, acetylated fatty acid glycerides, castor oil and other natural oils, Miglyol, fatty acid alcohols, cetyl alcohol, cetylstearyl alcohol or any combination thereof.

It is a further object of this invention to disclose such a material as defined in any of the above, wherein the proportion of the plasticizer is from 0 to 50%, preferably 0 to 35% of the hydrogel composition.

It is a further object of this invention to disclose such a material as defined in any of the above, wherein said water-soluble polymers are selected from a group consisting of polymerspolyethylene glycols, PVP, PVA, HPMC, HPC, hydroxyethylcelluloses (HEC), MC, carboxymethylcelluloses or their salts, dextrins, maltodextrins, cylcodextrins, dextrans urea, salts, sodium chloride, potassium chloride, ammonium chloride, sugars, sucrose, lactose, glucose, fructose, maltose, sugar alcohols, mannitol, sorbitol, xylitol, lactitol, or any combination thereof.

It is a further object of this invention to disclose such a material as defined in any of the above, wherein said swellable excipients are selected from a group consisting of polyvinylpyrrolidones, crospovidones, crosslinked sodium carboxymethylcellulose, crosslinked sodium carboxymethylstarch, polyethylene oxides, polymethyacrylates, low-substituted hydroxypropylmethylcellulose (L-HPC), cellulose acetate, ethylcellulose and polymethacrylates, high-molecular weight polyethylene oxides, xanthan gum, copolymers of vinylpyrrolidone and vinyl acetate, polyvinylpyrrolidones, crospovidones, crosslinked sodium carboxymethylcellulose, crosslinked sodium carboxymethylstarch, poly(hydroxyalkyl methacrylate), alginates and galactomannans and mixtures thereof or any combination thereof.

It is a further object of this invention to disclose such a material as defined in any of the above, wherein said reverse thermal gelaton compositions are selected from a group consisting of Poloxamers, Poloxamer 407 or any combination thereof.

It is a further object of this invention to disclose such a material as defined in any of the above, wherein said water-swellable matrix-forming polymers compositions are selected from a group consisting ohydroxy-propylmethylcelluloses (HPMC), hydroxyethylmethylcelluloses, hydroxypropylcelluloses (HPC), hydroxyethylcelluloses methylcelluloses (MC), ethylcelluloses, alkylcelluloses, hydroxy-alkylcelluloses hydroxyalkylmethylcelluloses, sodium carboxymethylcelluloses (NaCMC), alginates, galactomannans such as, for example, guar and carob flour, xanthans, polyethylene oxides, polyacrylic acids, polymethacrylic acids, polymethacrylic acid derivatives, polyvinyl alcohols (PVA), partially hydrolysed polyvinyl acetate (PVAc), polyvinylpyrrolidone (PVP), agar, pectin, gum arabic, tragacanth, gelatin, starch or starch derivatives or any combination thereof.

It is a further object of this invention to disclose such a material as defined in any of the above, wherein said material is administered orally, topically, intranasal, vaginally, rectal, ocular and parenteral routes.

It is a further object of this invention to disclose such a material as defined in any of the above, wherein said API is released at temperature of 36-42° C.; pH in the range of 5.5-8.0, at a rate of 80% in a time range of 3 to 30 hours.

It is a further object of this invention to disclose such a material as defined in any of the above, wherein said API is released at temperature of 36-42° C.; pH in the range of 1-8.0, at a rate of 80% in a time range of 2 hours to 4 weeks.

It is a further object of this invention to disclose such a material as defined in any of the above, wherein said API is dissolved, suspended and/or solid, amorphous or crystalline form.

It is a further object of this invention to disclose such a material as defined in any of the above, wherein said API is provided in various particle sizes, in unground, ground or in micronized form.

It is a further object of this invention to disclose such a material as defined in any of the above, wherein said material is administered topically; further wherein said API is selected from a group consisting of Antineoplastic drugs; Chemotherapeutic agents; Anti-infective agents, Antimicrobial drugs, Antiparasitic agents, Antivirals, Antihemorrhagics, Antithrombotic agents, antianemic drugs, Dermatologic drugs, antifungals, antiseptic, Genito-urinary system drugs, Gastrointestinal system, antiobesity, acid related disorders, Metabolism drugs, Anti-inflammatory product, Musculo-skeletal system acting drugs; Respiratory drugs, Otological drugs, Anti-infective drugs, Corticosteroids drugs, Analgesics drugs, GeneTherapy, Antiparasitics drugs, Growth factors, VEGF, Inhibitory factors, LIF or any combination thereof.

It is a further object of this invention to disclose such a material as defined in any of the above, wherein said material further comprising at least one selected from a group consisting of Poly(propylene oxide)—PPO, Poly(lactide-co-glycolic acid)—PLGA, Poly(N-isopropylacrylamide)—PNIPAM, Poly(propylene fumerate)—PPF, Poly(urethane)—PU, Poly(organophosphazene)—POP, Poloxamers of the type PEO-PPO-PEO (Poly(ethylene oxide), Poly (propylene oxide), Poly(ethylene oxide)) such as poloxamer 68, 88, 98, 108, 124, 127, 188, 237, 338 and 407, Stearic Acid, Poly(acrilic acid), Glyceryl Stearate, Cetearyl Alcohol, Sodium Stearoyl Lactylate, Hydroxy-Lenolin or any combination thereof.

It is a further object of this invention to disclose such a material, wherein said material is used as biological glue.

It is a further object of this invention to disclose a method for administering a therapeutic agent to the internal surface of an internal body cavity, comprising:

- incorporating an effective amount of said therapeutic agent into a biocompatible sustained-release material;
- inflating a balloon to open said internal body cavity to a substantially symmetrical shape;
- introducing said biocompatible sustained-release material into said internal body cavity;
- applying said biocompatible sustained-release material to at least part of the internal surface of said internal body cavity;
- applying force to said material, thereby spreading it over at least part of the internal surface of said internal cavity;
- causing said biocompatible sustained-release material to adhere to said internal surface of said internal body cavity; and,
- releasing said therapeutic agent into said internal body cavity.

It is a further object of this invention to disclose such a method as defined in any of the above, additionally comprising step of providing said material with at least one active ingredient (API).

It is a further object of this invention to disclose such a method as defined in any of the above, wherein said material comprises excipients selected from acids or buffer substances adapted to modify the pH so as to reduce the dependence of said release of active ingredient on the pH of the release medium.

It is a further object of this invention to disclose such a method as defined in any of the above, additionally comprising step of providing said material with at least one more compounds selected from adhesive and thickening compounds; bonding agents; pH-modifying substances; diffusion coating; plasticizers; matrix permeability increasing components; swellable excipients matrix-forming polymers; diffusion-controlled or pulsatile formulations; reverse thermal gelaton agents or any combination thereof.

It is a further object of this invention to disclose such a method as defined in any of the above, wherein said adhesive and thickening compounds are selected from a group consisting of polycarbophil, acrylic acid crosslinked, divinyl glycol, hydroxypropylmethylcellulose (HPMC), polyvinylpyrrolidone (PVP), methylcellulose (MC), hydroxy-propylcellulose (HPC), other hydroxyalkylcelluloses, hydroxyalkylmethylcelluloses, carboxy-methylcelluloses and salts thereof, polyacrylic acids, polymethacrylates, gelatin, starch or starch derivatives, as well as gums like guar gum and xanthan gum or any combination thereof.

It is a further object of this invention to disclose such a method as defined in any of the above, wherein said bonding agents are selected from a group consisting of polycarbophil, cellulose, microcrystalline cellulose, cellulose derivatives such as, for example, HMPC, HPC and low-substituted hydroxypropylcellulose (L-HPC), dicalcium phosphate, lactose, PVP and sucrose, ethylcellulose, hydroxypropymethylcellulose acetate succinate (HPMCAS), PVP, vinylpyrrolidone/vinyl acetate copolymer, polyethylene glycol, polyethylene oxide, polymethacrylates, polyvinyl alcohols (PVA), partially hydrolysed polyvinyl acetate (PVAc), polysaccharides (e.g. alginic acid, alginates, galactomannans) waxes, fats and fatty acid derivatives or any combination thereof.

It is a further object of this invention to disclose such a method as defined in any of the above, wherein said pH-modifying substances are selected from a group consisting of acids, bases and buffer, adipic acid, malic acid, L-arginine, ascorbic acid, aspartic acid, benzenesulphonic acid, benzoic acid, succinic acid, citric acid, ethanesulphonic acid, 2-hydroxyethanesulphonic acid, fumaric acid, gluconic acid, glucuronic acid, glutamic acid, potassium hydrogen tartrate, maleic acid, malonic acid, methanesulphonic acid, toluenesulphonic acid, trometamol, tartaric acid. Citric acid, succinic acid, tartaric acid, potassium hydrogen tartrate are preferably employed or any combination thereof.

It is a further object of this invention to disclose such a method as defined in any of the above, wherein said diffusion coating are selected from a group consisting of ethylcelluloses and polymethacrylates such as, for example, EUDRAGIT® NE, EUDRAGIT® RS and RL, cellulose acetate and cellulose acetate butyrate or any combination thereof.

It is a further object of this invention to disclose such a method as defined in any of the above, wherein said plasticizers are selected from a group consisting of citric acid derivatives, triethyl citrate, tributyl citrate, acetyl triethyl citrate, phthalic acid derivatives, dimethyl phthalate, diethyl phthalate, dibutyl phthalate, benzoic acid and benzoic esters, other aromatic carboxylic esters, trimellithic esters, aliphatic dicarboxylic esters, dialkyl adipates, sebacic esters, in particular diethyl sebacate, tartaric esters, glycerol monoacetate, glycerol diacetate or glycerol triacetate, polyols, glycerol, 1,2-propanediol, polyethylene glycol of varying chain length, fatty acids and derivatives, glycerol monostearates, acetylated fatty acid glycerides, castor oil and other natural oils, Miglyol, fatty acid alcohols, cetyl alcohol, cetylstearyl alcohol or any combination thereof.

It is a further object of this invention to disclose such a method as defined in any of the above, wherein the proportion of the plasticizer is from 0 to 50%, preferably 0 to 35% of the hydrogel composition.

It is a further object of this invention to disclose such a method as defined in any of the above, wherein said water-soluble polymers are selected from a group consisting of polymerspolyethylene glycols, PVP, PVA, HPMC, HPC, hydroxyethylcelluloses (HEC), MC, carboxymethylcelluloses or their salts, dextrins, maltodextrins, cylcodextrins, dextrans urea, salts, sodium chloride, potassium chloride, ammonium chloride, sugars, sucrose, lactose, glucose, fructose, maltose, sugar alcohols, mannitol, sorbitol, xylitol, lactitol, or any combination thereof.

It is a further object of this invention to disclose such a method as defined in any of the above, wherein said swellable excipients are selected from a group consisting of polyvinylpyrrolidones, crospovidones, crosslinked sodium carboxymethylcellulose, crosslinked sodium carboxymethylstarch, polyethylene oxides, polymethyacrylates, low-substituted hydroxypropylmethylcellulose (L-HPC), cellulose acetate, ethylcellulose and polymethacrylates, high-molecular weight polyethylene oxides, xanthan gum, copolymers of vinylpyrrolidone and vinyl acetate, polyvinylpyrrolidones, crospovidones, crosslinked sodium carboxymethylcellulose, crosslinked sodium carboxymethylstarch, poly(hydroxyalkyl methacrylate), alginates and galactomannans and mixtures thereof or any combination thereof.

It is a further object of this invention to disclose such a method as defined in any of the above, wherein said reverse thermal gelaton compositions are selected from a group consisting of Poloxamers, in particular Poloxamer 407 or any combination thereof.

It is a further object of this invention to disclose such a method as defined in any of the above, wherein said water-swellable matrix-forming polymers compositions are selected from a group consisting ohydroxy-propylmethylcelluloses (HPMC), hydroxyethylmethylcelluloses, hydroxypropylcelluloses (HPC), hydroxyethylcelluloses methylcelluloses (MC), ethylcelluloses, alkylcelluloses, hydroxy-alkylcelluloses hydroxyalkylmethylcelluloses, sodium carboxymethylcelluloses (NaCMC), alginates, galactomannans such as, for example, guar and carob flour, xanthans, polyethylene oxides, polyacrylic acids, polymethacrylic acids, polymethacrylic acid derivatives, polyvinyl alcohols (PVA), partially hydrolysed polyvinyl acetate (PVAc), polyvinylpyrrolidone (PVP), agar, pectin, gum arabic, tragacanth, gelatin, starch or starch derivatives or any combination thereof.

It is a further object of this invention to disclose such a method as defined in any of the above, additionally comprising step of administering said material orally, topically, intranasal, vaginally, rectal, ocular and parenteral routes or any combination thereof.

It is a further object of this invention to disclose such a method as defined in any of the above, wherein said API is released at temperature of 36-42° C.; pH in the range of 5.5-8.0, at a rate of 80% in a time range of 3 to 30 hours.

It is a further object of this invention to disclose such a method as defined in any of the above, wherein said API is released at temperature of 36-42° C.; pH in the range of 1-8.0, at a rate of 80% in a time range of 2 to 4 weeks.

It is a further object of this invention to disclose such a method as defined in any of the above, wherein said API is released at temperature of 36-42° C.; pH in the range of 1-9.0, at a rate of 80% in a time range of 3 to 30 hours.

It is a further object of this invention to disclose such a method as defined in any of the above, wherein said API is dissolved, suspended and/or solid, amorphous or crystalline form.

It is a further object of this invention to disclose such a method as defined in any of the above, wherein said API is provided in various particle sizes, in unground, ground or in micronized form.

It is a further object of this invention to disclose such a method as defined in any of the above, wherein said material is administered topically; further wherein said API is selected from a group consisting of Antineoplastic drugs; Chemotherapeutic agents; Anti-infective agents, Antimicrobial drugs, Antiparasitic agents, Antivirals; Drugs acting on the blood and blood forming organs, Antihemorrhagics, Antithrombotic agents, antianemic drugs, Dermatologic drugs, antifungals, antiseptic, Genito-urinary system drugs, Gastrointestinal system, antiobesity, acid related disorders, Metabolism drugs, Anti-inflammatory product, Musculo-skeletal system acting drugs; Neurological drugs, Respiratory drugs, Cardio-vascular drugs, Otological drugs, Anti-infective drugs, Corticosteroids drugs, Analgesics and anesthetics drugs, GeneTherapy, Antiparasitics drugs, Growth factors, VEGF, Inhibitory factors, LIF or any combination thereof.

It is a further object of this invention to disclose such a method as defined in any of the above, additionally comprising step of providing said material with at least one selected from a group consisting of Poly(propylene oxide)—PPO, Poly(lactide-co-glycolic acid)—PLGA, Poly(N-isopropylacrylamide)—PNIPAM, Poly(propylene fumerate)—PPF, Poly(urethane)—PU, Poly(organophosphazene)—POP, Poloxamers of the type PEO-PPO-PEO (Poly(ethylene oxide), Poly(propylene oxide), Poly(ethylene oxide)) such as poloxamer 68, 88, 98, 108, 124, 127, 188, 237, 338 and 407, Stearic Acid, Poly(acrilic acid), Glyceryl Stearate, Cetearyl Alcohol, Sodium Stearoyl Lactylate, Hydroxy-Lenolin or any combination thereof.

It is a further object of this invention to disclose such a method, wherein said biocompatible sustained-release material is the biocompatible sustained-release material as defined in any of the above.

It is a further object of this invention to disclose such a method as defined in any of the above, wherein said internal body cavity is at least one selected from a group of internal cavities that includes, among others, the urinary bladder, mouth, nasal and paranasal sinus, gallbladder, esophagus, rectum, lungs, vagina, uterus, stomach, renal pelvis, pleura, abdomen, peritoneum, pelvis, liver, kidney, heart, intestine, brain, vertebral column, etc.

It is a further object of this invention to disclose such a method as defined in any of the above, wherein said therapeutic agent is a therapeutic agent for treatment of superficial bladder cancer.

It is a further object of this invention to disclose such a method as defined in any of the above, wherein said step of introducing said biocompatible sustained-release material into said internal body cavity further comprises a step of introducing said biocompatible sustained-release material into said internal body cavity via a catheter.

It is a further object of this invention to disclose such a method as defined in any of the above, wherein said step of releasing said therapeutic material into said internal body cavity further comprises a step of dissolving said biocompatible sustained-release material in body fluid within said internal body cavity, whereby said therapeutic agent is released from said biocompatible sustained-release material.

It is a further object of this invention to disclose such a method as defined in any of the above, wherein said step of applying force to said material further comprises a step of filling said catheter balloon with water and positioning the patient to utilize the gravitational forces directly toward the target tissue during the solidification of the material and cause optimal adhesion to that target tissue.

It is a further object of this invention to disclose such a method as defined in any of the above, wherein said step of applying gravitational force to said material further comprises a step of changing the position of the patient before applying partial doses of material to enable substantially full coating of the whole targeted internal cavity surface.

It is a further object of this invention to disclose such a method as defined in any of the above, wherein said step of applying force to said material further comprises a step of filling said balloon with a liquid denser than water.

It is a further object of this invention to disclose such a method, wherein said liquid denser than water comprises a solution of salt in water, said solution having a density greater than 1.0 g/cm$^3$.

It is a further object of this invention to disclose such a method, wherein said liquid denser than water comprises a solution of glucose in water, said solution having a density greater than 1.0 g/cm$^3$.

It is a further object of this invention to disclose such a method as defined in any of the above, wherein said step of applying force to said material further comprises steps of inserting a first magnetic means into said balloon; and, applying a second magnetic means such that the magnetic attraction of said first magnetic means and said second magnetic means causes said first magnet to move within said balloon, whereby said attraction applies force to at least part of the internal surface of said internal cavity.

It is a further object of this invention to disclose such a method as defined in any of the above, wherein said step of applying force to said material further comprises steps of introducing a ferromagnetic liquid into said balloon; and, applying magnetic means such that the magnetic attraction of said magnetic means and ferromagnetic particles suspended within said ferromagnetic liquid causes said ferromagnetic particles to move within said balloon, thereby applying force to at least part of the internal surface of said internal cavity.

It is a further object of this invention to disclose such a method as defined in any of the above, wherein said step of applying force to said material further comprises steps of introducing into said balloon a substance chosen from (a) a constant or electric magnet, (b) a piece of ferromagnetic material, and (c) a ferromagnetic liquid;

placing the patient within an MRI apparatus; and, activating said MRI apparatus such that the magnetic field of said MRI apparatus causes said substance to move within said balloon, thereby applying force to at least part of said internal cavity.

It is a further object of this invention to disclose such a method as defined in any of the above, wherein the solubility of said material is sufficiently high that said material will completely degrade in less than 4 weeks after incorporation into an internal body cavity.

It is a further object of this invention to disclose such a method as defined in any of the above, wherein said material is characterized by a viscosity of less than 200 Pa·s at a range of 10° C. to 25° C. and greater than 3000 Pa·s at a range of 35° C.-37° C.

It is a further object of this invention to disclose such a method as defined in any of the above, wherein said material is characterized by a viscosity of less than 200 Pa·s at 10° C. and greater than 3000 Pa·s at 37° C.

It is a further object of this invention to disclose such a method as defined in any of the above, wherein the instillation temperature of said material is between 4° C. and 60° C.

It is a further object of this invention to disclose such a method as defined in any of the above, wherein said material comprising 20-30% Pluronic F-127; 0-1.8% PEG-400; 0.1%-0.3% HPMC; an effective amount of a therapeutic agent; and the balance water.

It is a further object of this invention to disclose such a method as defined in any of the above, wherein said material comprising 20-30% Pluronic F-127; 0-2.5% PEG-400; 0.05%-0.5% HPMC; an effective amount of a therapeutic agent; and the balance water.

It is a further object of this invention to disclose such a method as defined in any of the above, additionally comprising step of providing said material as biological glue.

It is a further object of this invention to disclose such a method as defined in any of the above, wherein the weight of the balloon filled with a liquid denser than water is used for the application of the gel (utilizing its gravity).

BRIEF DESCRIPTION OF THE FIGURES

The invention disclosed herein is described with reference to the figures, in which:

FIG. 5 presents graphs representing results of measurements of rheological parameters of the material according to several embodiments of the invention herein disclosed.

DETAILED DESCRIPTION OF THE PREFERRED EMBODIMENTS

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

As used herein, the term "internal cavity" is used to describe parts in the body that are either accessible through an orifice—e.g., mouth, bladder, intestine, esophagus, rectum, lungs, vagina, stomach, renal pelvis, etc.—or by way of minimally invasive, surgery—e.g., pleura, abdomen, peritoneum, pelvis, etc. The definition includes artificially made or enlarged cavities in adipose tissues and fibrous capsules in internal organs such as the kidney, heart, intestine, etc. that are accessible by image guided laparoscopic techniques.

As used herein, the term "DTC" is used to refer generically to the materials disclosed in the present invention. The terms "DTCx" and "DTC-n" (where n is an integer) are used to refer to particular embodiments, either generically (DTCx) or specifically (e.g. DTC-2).

The present invention provides a bioerodible, biocompatible gel mixed with an active agent, such as chemotherapy agent like MMC or gemcitabine, or immunotherapy such as BCG (bacillus Calmette-Guérin), which is inserted into the upper urinary tract via a designated catheter, solidifies and forms a drug reservoir at the destined treatment area such as the renal pelvis. The diffusion of the drug from the gel and the erosion of the gel by the urine or the biodegradability of the gel, deliver drug to the tissue—producing prolonged high topical drug concentration but low systemic exposure. This, the system increases bioavailability, reduces toxicity and improves treatment efficacy. Furthermore, loading the material with significant concentration of chemotherapy agent and applying the material directly over a tumor for a prolonged duration, may ablate non-resected tumors that are in close contact with the material.

Figure 1:
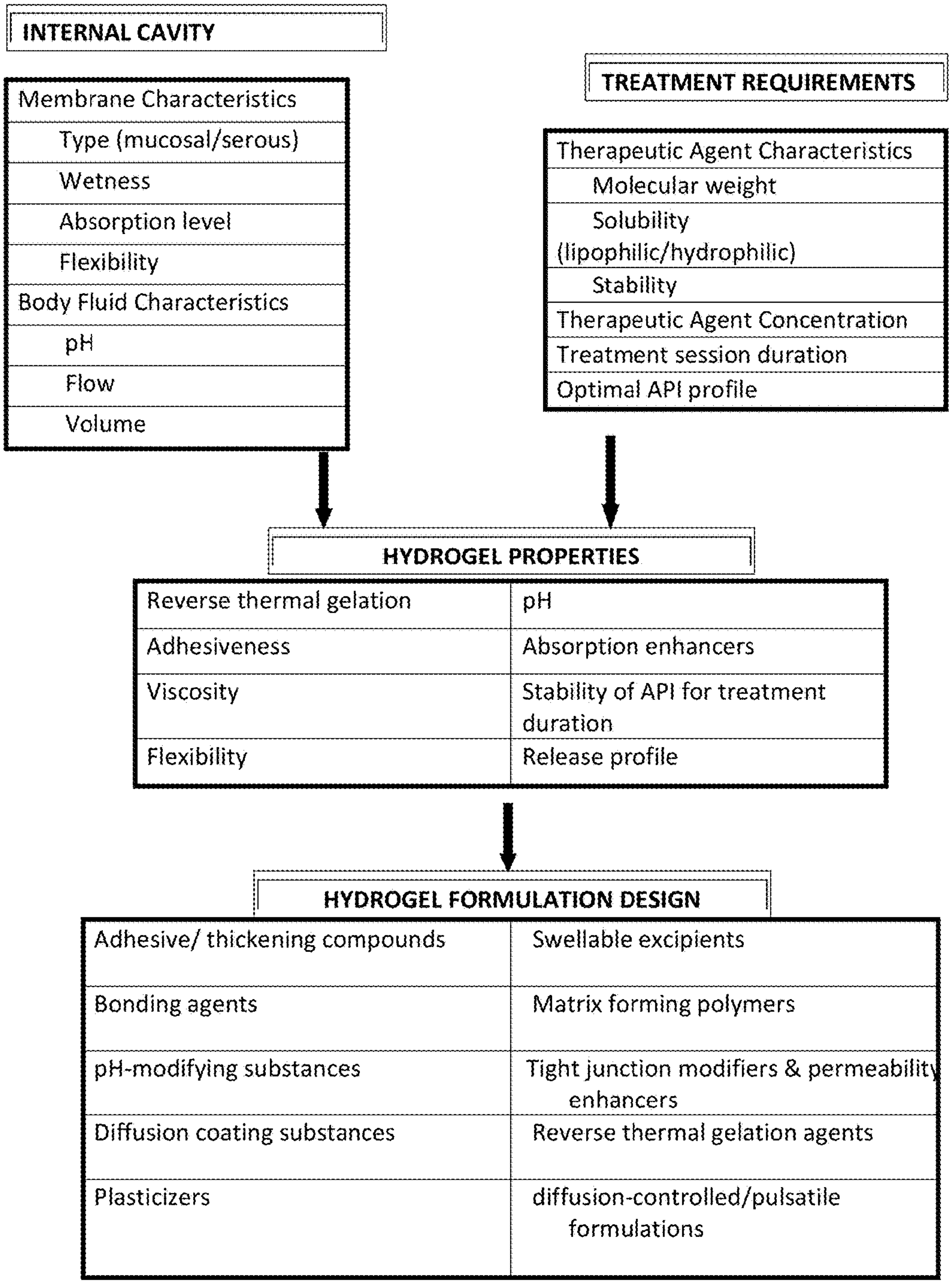
FIG. 1 presents a flow diagram of the creation of a hydrogel composition in a drug delivery system for treatment of internal cavities.

The present invention provides a design of such gel compositions that is based on the characteristics of the internal cavities to be treated and the specific requirements for said treatments in order to determine the required properties of hydrogel systems that can satisfy all these requirements. A flow diagram for creation of hydrogel composition is illustrated in FIG. 1. This structured set of gel properties enables the formulation of gel systems for optimal drug delivery. The present invention provides a structured design and test flow that assures optimal hydrogels for optimal treatments.

In some embodiments, the present invention additionally provides a bioerodible, biocompatible hydrogel that that is mixed with a neurological drug such as botulinum toxin, is inserted into the bladder, solidifies and forms a drug reservoir inside the bladder. The erosion of the material in the urine, promotes topical drug delivery and increases the drug affinity to the bladder wall tissue producing high topical drug concentration in the bladder wall and at the same time keeps a low systemic exposure. The system provides drug delivery to the entire bladder resulting in total tissue contact with the delivered neurological drug as opposed to delivery induced by local injections.

The invented material includes a mixture of hydrogel with botulinium toxin (A, B, C1, D, E, F and G and equivalent neurological drugs) for the treatment of disorders characterized by bladder spasms (eg. urge incontinence due to unstable bladder or unstable detrusor, sphincter or neurogenic bladder, etc.). The hydrogel mixed with botulinium toxin will be instilled into the bladder without injections into the bladder tissue and its effect will be.

The present invention also includes the use of the novel pharmaceutical formulation or admix for producing medicaments which are intended for the treatment and/or prevention of disorders in humans. These systems contain drugs embedded in a slowly degrading biocompatible admix and are combined with administering means, so that the materials can be introduced in a minimally invasive manner into a body cavity and provide a prolonged exposure of the cavity tissue to the drug, thus improving the treatment efficacy in terms of improved therapeutic effect of the drug and reduced tissue damage. The admix/mixture is biocompatible and dissolves in body fluids such as urine, serous fluids or lymphatic fluids, and then it is expelled from the body.

The aim of the prolonged exposure of target tissue to drugs released from the coating is to enhance the efficacy of the drug in topical treatment of that target tissue, while reducing potential systemic adverse effects to other organs. As a specific example, the aim of the prolonged exposure of cancer cells to an anticancer drug released from the coating is to enhance the efficacy of the drug in killing cancer cells and, therefore, potentially reduce the recurrence rate of cancer tumors, while reducing the systemic effect of chemotherapy on other parts of the patient body.

The homogeneous coating obtained in the invention disclosed herein, i.e., a solidified, unified and homogeneous layer that provides continuous sustained release of therapeutic agents upon the inner surface of an internal body cavity, as herein disclosed, has to the inventors' knowledge never been produced or used clinically.

Thus, it is one object of the present invention to provide a material that includes active pharmaceutical ingredients (APIs) as a part of its basic formulation.

The current invention provides a platform for the redesign of drugs to make them suitable for topical administration. Company studies demonstrated solubility and first order sustained release of Mytomicin C, Doxorubicin and Gemcitabin (groups 1 & 2), Abamectin (group 3), exogenous glycosaminoglycan, group 4), Naproxen (group 5), lidocaine and voltaren (group 6).

Among the drugs that can be administered topically are drugs that belong to the following families:

1. Antineoplastic drugs
2. Chemotherapeutic agents
3. Anti-infective agents (e.g. Antimicrobial drugs, Antiparasitic agents, Antivirals)
4. Genito-urinary system drugs
5. Anti-inflammatory products
6. Analgesics
7. Musculoskeletal system acting drugs
8. Drugs acting on the blood and blood forming organs (Antihemorrhagics, Antithrombotic agents, antianemic drugs)
9. Dermatologic drugs (antifungals, antiseptic)
10. Gastrointestinal system (antiobesity, acid related disorders)
11. Metabolism drugs
12. Neurological drugs
13. Respiratory drugs including nasal drugs
14. Cardio-vascular drugs
15. Otological drugs
16. Anti-infective drugs
17. Corticosteroids drugs
18. Analgesics drugs
19. Antiparasitics drugs
20. Anasthetic Drugs In other cases, the topical treatment is just evolving:

21. Growth factor (e.g., for treatment of heart muscle ischemia)
22. Gene Therapy agents
23. Mucin
24. Hyaluronic Acid Drugs can be embedded as part of the invented materials as a single therapeutic agent or as a combination. As an example, a mixture containing exogenous glycosaminoglycan and Naproxen can be combined in a specific material for the treatment of interstitial cystitis for alleviating the inflammation symptoms and replacing the damaged mucosal lining of the urinary bladder cavity that is typical for this disease.

The present invention provides a formulation/mixture which release active ingredients (API) in a controlled fashion over a prolonged period. It is further an object of the present invention to provide medicament formulations with particular release profiles through which the prior art problems. As an example an average release rate between 80% in 6 hours and 80% in 24 hours is maintained.

As standard, chemotherapy drugs are administered at a maximal concentration level that is tolerable by patients. The present invention study results demonstrate that a further improvement in efficacy can be gained by increasing the exposure time to chemotherapy drugs. This is at the core of the present invention.

In addition, the use of such formulation allows reduction of the frequency of administration thus leads to improved patient's compliance.

A longer exposure time of the API has distinct advantages and it is expected that a prolonged exposure with an API on use of a medicament with controlled release of active ingredient makes it possible to prolong substantially the time window in which improved therapy can be achieved. The use of the novel medicinal forms with controlled release of active ingredient is expected to achieve substantially more constant drug levels and avoid the occurrence of level peaks, thus improving for example the therapeutic efficacy and reducing the frequency and intensity of unwanted side effects.

In addition, the use of such admix/formulation/mixture allows the frequency of administration to be reduced and thus leads to improved acceptance and compliance by the patient.

It is expected as well that controlled-release of APIs prolong exposure without the occurrence of an increase in side effects, an adverse effect on reliability and safety of therapies. According to a preferred embodiment of the present invention the admix/formulation/mixture described above, is for example in the form of active ingredient-containing hydrogels. These diffusion-controlled systems may be completely diluted in the hydrogel admix/formulation/mixture or can be multiparticulate, i.e. they may consist of a large number of coated cores such as, for example, of microencapsulated APIs, where appropriate together with conventional excipients and carriers, as defined below for example, is applied and subsequently coated with a diffusion coating which may comprise plasticizers and other excipients. The diffusion-controlled systems according to the invention may additionally consist of homogeneous active ingredient-containing cores which are produced for example by granulation, rotor granulation, fluidized bed agglomeration, tableting, wet extrusion or melt extrusion, where appropriate with spheronization, and are coated with a diffusion coating which may comprise plasticizers and other excipients.

According to one embodiment, the present invention may provide a combination of APIs, one or more diluted or suspended in the gel and one or more microencapsulated for slower release effect. For example, an anesthetic like lidocaine dissolved in the admix/formulation/mixture for immediate anesthetic effect and encapsulated MMC for cancer treatment that is released after the bladder wall is insensitive and the patient can stand the MMC therapy.

In a preferred embodiment of this invention, the active ingredient-containing particles comprise excipients such as, for example, acids or buffer substances which modify the pH and thus contribute to reducing the dependence of the release of active ingredient on the pH of the release medium.

According to a preferred embodiment of the present invention the material/formulation/mixture described above, additionally comprises at least one ingredient selected from:

(a) adhesive and thickening compounds;
(b) bonding agents;
(c) pH-modifying substances;
(d) diffusion coating;
(e) plasticizers;
(f) Tight junction modifiers & permeability enhancers;
(g) matrix permeability increasing components;
(h) swellable excipients matrix-forming polymers;
(i) diffusion-controlled or pulsatile formulations; and,
(j) reverse thermal gelation agents.

The adhesive and thickening compounds preferably used in the production of coated neutral pellets (e.g. consisting of sucrose, microcrystalline cellulose, citric acid) are polycarbophil (polymer of acrylic acid crosslinked with divinyl glycol), hydroxypropylmethylcellulose (HPMC) and polyvinylpyrrolidone (PVP). It is likewise possible to employ other naturally, synthetic or partially synthetic polymers such as, for example methylcellulose (MC), hydroxy-propylcellulose (HPC), other hydroxyalkylcelluloses and hydroxyalkylmethylcelluloses, carboxy-methylcelluloses and salts thereof, polyacrylic acids, polymethacrylates, gelatin, starch or starch derivatives, as well as gums like guar gum and xanthan gum.

The bonding agents employed for the production of active ingredient-containing microcapsules are for example polycarbophil, cellulose, microcrystalline cellulose, cellulose derivatives such as, for example, HMPC, HPC and low-substituted hydroxypropylcellulose (L-HPC), dicalcium phosphate, lactose, PVP and sucrose, ethylcellulose, hydroxypropymethylcellulose acetate succinate (HPMCAS), PVP, vinylpyrrolidone/vinyl acetate copolymer, polyethylene glycol, polyethylene oxide, polymethacrylates, polyvinyl alcohols (PVA), partially hydrolysed polyvinyl acetate (PVAc), polysaccharides (e.g. alginic acid, alginates, galactomannans) waxes, fats and fatty acid derivatives. The pH-modifying substances such as, for example, acids, bases and buffer substances are incorporated into the active ingredient-containing core. Addition of these substances makes it possible to reduce markedly the pH-dependence of the release of the APIs. Examples of suitable excipients which modify the pH in the active ingredient-containing cores are: adipic acid, malic acid, L-arginine, ascorbic acid, aspartic acid, benzenesulphonic acid, benzoic acid, succinic acid, citric acid, ethanesulphonic acid, 2-hydroxyethanesulphonic acid, fumaric acid, gluconic acid, glucuronic acid, glutamic acid, potassium hydrogen tartrate, maleic acid, malonic acid, methanesulphonic acid, toluenesulphonic acid, trometamol, tartaric acid. Citric acid, succinic acid, tartaric acid, potassium hydrogen tartrate are preferably employed. Particularly suitable for producing the diffusion coating are ethylcelluloses and polymethacrylates such as, for example, EUDRAGIT® NE, EUDRAGIT® RS and RL. However, other materials such as, for example, cellulose acetate and cellulose acetate butyrate can also be employed as film-forming diffusion-controlling polymers. Examples of plasticizers used are citric acid derivatives (e.g. triethyl citrate, tributyl citrate, acetyl triethyl citrate), phthalic acid derivatives (e.g. dimethyl phthalate, diethyl phthalate, dibutyl phthalate), benzoic acid and benzoic esters, other aromatic carboxylic esters (e.g. trimellithic esters), aliphatic dicarboxylic esters (e.g. dialkyl adipates, sebacic esters, in particular diethyl sebacate, tartaric esters), glycerol monoacetate, glycerol diacetate or glycerol triacetate, polyols (e.g. glycerol, 1,2-propanediol, polyethylene glycol of varying chain length), fatty acids and derivatives (e.g. glycerol monostearates, acetylated fatty acid glycerides, castor oil and other natural oils, Miglyol) and fatty acid alcohols (e.g. cetyl alcohol, cetylstearyl alcohol).

The nature and amount of the plasticizer are chosen so that the above-defined release according to the invention and the necessary stability of the medicinal forms is achieved. The proportion of the plasticizer is from 0 to 50%, preferably 0 to 35%, particularly preferably 0 to 25% based on the mass of the hydrogel composition.

The release rate according to the invention is controlled by the gel composition. Certain components may increase the permeability of the admix/formulation/mixture including water-soluble polymers such as, for example, polyethylene glycols, PVP, PVA, HPMC, HPC, hydroxyethylcelluloses (HEC), MC, carboxymethylcelluloses or their salts, dextrins, maltodextrins, cylcodextrins, dextrans or other soluble substances such as, for example, urea, salts (sodium chloride, potassium chloride, ammonium chloride, etc.), sugars (sucrose, lactose, glucose, fructose, maltose etc.) and sugar alcohols (mannitol, sorbitol, xylitol, lactitol, etc.). Based on the mass of the hydrogel, the amount of the water-soluble polymers ranges from 0 to 50%, preferably 0 to 35%, particularly preferably 0 to 20%, increasing permeability components may be employed.

A further aspect of the present invention are coated admix/formulation/mixture which comprise one or more swellable excipients which, on penetration of liquid through the membrane, swell greatly and, through the swelling and volume expansion, cause the coating to split. The splitting of the coating makes it possible for the medicinal substance to be released from the admix/formulation/mixture, usually in pulsatile form. Swellable excipients which these formulations may comprise are, for example, polyvinylpyrrolidones, crospovidones, crosslinked sodium carboxymethylcellulose, crosslinked sodium carboxymethylstarch, polyethylene oxides, polymethyacrylates, low-substituted hydroxypropylmethylcellulose (L-HPC). Examples of suitable coating materials are cellulose acetate, ethylcellulose and polymethacrylates.

The described diffusion-controlled or pulsatile formulations can be employed directly and unmodified as medicinal form. However, they may also be further processed, where appropriate with addition of excipients, to the final admix/formulation/mixture. In order to achieve a desired release profile it is also possible to combine different coated formulations in one medicinal form, and administration of an initial dose can take place for example by combination with rapid-release formulation particles, e.g. uncoated pellets, granules or powder.

In a further embodiment of the admix/formulation/mixture containing the controlled release ingredient. These so-called admix/formulation/mixture release the active ingredient by diffusion and/or erosion.

The mass ratio of active ingredient to the total mass of the admix/formulation/mixture in these novel formulations is in the range from 1:1 to 1:10,000, preferably in the range from 1:2 to 1:1,000.

admix/formulation/mixture which can be employed are water-soluble, water-swellable or water-insoluble substances. The novel formulations preferably comprise one or more water-swellable polymers.

A preferred family of candidates to be utilized as a basis for obtaining said hydrogel is group of tri-block copolymers designated as PEG-PPG-PEG (PEG=Polyethylene glycol and PPG=Polypropylene glycol) and called Poloxamers, that produce reverse thermal gelaton compositions, i.e., with the characteristic that their viscosity increases with increasing temperature up to a point from which viscosity again decreases. In particular, Poloxamer 407 possesses a gelling temperature which is above 10° C. but below the human body temperature, i.e., 37° C. This characteristic may confer the ability of a composition containing the compound to be injected or infused in liquid state into a bodily inner cavity at a low temperature and, afterwards, as the composition warms, it solidifies into a gel, thus stabilizing upon the wall of the inner body cavity.

This characteristic has allowed Poloxamer 407 (PF-127) to be used as a carrier for most routes of administration including oral, topical, intranasal, vaginal, rectal, ocular and parenteral routes.

Poloxamer 407 (PF-127) is a nonionic surfactant composed of polyoxyethylene-polyoxypropylene triblock copolymers in a concentration ranging from 20-30%. At low concentrations ($10^{-4}$-$10^{-5}$%) they form monomolecular micelles, but higher concentrations result in multimolecular aggregates consisting of a hydrophobic central core with their hydrophilic polyoxyethylene chains facing the external medium. Micellization occurs in dilute solutions of block copolymers in selected solvents above the critical micellar concentration, at a given temperature. At higher concentrations, above a critical gel concentration, the micelles can order into a lattice.

Aqueous solutions of poloxamers are stable in the presence of acids, alkalis, and metal ions. Commonly used poloxamers include the 88 (F-68 grade), 237 (F-87 grade), 338 (F-108 grade) and 407 (F-127 grade) types, which are freely soluble in water. The "F" designation refers to the flake form of the product. PF-127 has a good solubilizing capacity, low toxicity and is, therefore, considered a good medium for drug delivery systems.

PF-127 is a commercially available polyoxyethylene-polyoxypropylene triblock copolymer that possesses a general formula E106 P70 E106, with an average molar mass of 13,000. It contains approximately 70% ethylene oxide, which accounts for its hydrophilicity. It is one of the series of poloxamer ABA block copolymers. As said above, PF-127 aqueous solutions of 20 to 30% w/w have the interesting characteristic of reverse thermal gelation, i.e., they are liquid at refrigerated temperatures (4-5° C.), but gel upon warming to room temperature. The gelation is reversible upon cooling. This phenomenon, therefore, suggests that when poured onto the skin or injected into a body cavity, the gel preparation will form a solid artificial barrier and a sustained release depot. Furthermore, PF-127 has been reported to be the least toxic of commercially available copolymers.

Water-soluble or water-swellable matrix-forming polymers preferably employed are hydroxy-propylmethylcelluloses (HPMC), hydroxyethylmethylcelluloses, hydroxypropylcelluloses (HPC), hydroxyethylcelluloses methylcelluloses (MC), ethylcelluloses, other alkylcelluloses, hydroxy-alkylcelluloses and hydroxyalkylmethylcelluloses, sodium carboxymethylcelluloses (NaCMC), alginates, galactomannans such as, for example, guar and carob flour, xanthans, polyethylene oxides, polyacrylic acids, polymethacrylic acids, polymethacrylic acid derivatives, polyvinyl alcohols (PVA), partially hydrolysed polyvinyl acetate (PVAc), polyvinylpyrrolidone (PVP), agar, pectin, gum arabic, tragacanth, gelatin, starch or starch derivatives and mixtures of these substances.

In this connection, the admix/formulation/mixture according to the invention should preferably comprise at least 0.1-2.0% of a hydroxypropylmethylcellulose type whose nominal viscosity (measured as 2% strength aqueous solution at 20° C.) is at least 0.015 Pa s, preferably at least 0.050 Pa s. HPMC types preferably used have a degree of substitution of methoxy groups of 16.5-30%, particularly preferably 19-30%, and a degree of substitution of hydroxypropoxy groups of 4-32%, particularly preferably 4-12%.

In a particularly preferred embodiment of this invention, substances which control the pH in the admix/formulation/mixture are incorporated into the admix/formulation/mixture. The addition of such pH-modifying excipients and/or the addition of substances which dissolve or are dissolved out of the admix/formulation/mixture as the pH increases, and thus increase the porosity or permeability of the admix/formulation/mixture and/or promote erosion of the admix/formulation/mixture, makes it possible to achieve a virtually pH-independent release for these preferred embodiments of the present invention.

Examples of suitable excipients which can be added to the admix/formulation/mixture according to the invention to achieve release which is as far as possible pH-independent are the following substances: adipic acid, malic acid, L-arginine, ascorbic acid, aspartic acid, benzenesulphonic acid, benzoic acid, succinic acid, cellulose phthalates, in particular cellulose acetate phthalate and hydroxypropylmethylcellulose phthalate, cellulose succinates, in particular cellulose acetate succinate and HPMCAS, citric acid, ethanesulphonic acid, 2-hydroxyethanesulphonic acid, fumaric acid, gluconic acid, glucuronic acid, glutamic acid, potassium hydrogen tartrate, maleic acid, malonic acid, methanesulphonic acid, polymethacrylates (e.g. EUDRAGIT® types), toluenesulphonic acid, trometamol, tartaric acid. Citric acid, succinic acid, tartaric acid, HPMCAS, and polymethacrylates (e.g. EUDRAGIT® L) are preferably employed. If these excipients are present in the admix/formulation/mixture according to the invention, they are typically added in a proportion of from 10 to 50% based on the total mass of the admix/formulation/mixture.

Examples of plasticizing excipients in the hydrogel formulation are propylene glycol, glycerol, triethylene glycol, butanediols, pentanols, such as pentaerythritol, hexanols, long-chain alcohols, polyethylene glycols, polypropylene glycols, polyethylene/propylene glycols, silicones, phthalic acid derivatives (e.g. dimethyl phthalate, diethyl phthalate, dibutyl phthalate), benzoic acid and benzoic esters, other aromatic carboxylic esters (e.g. trimellithic esters), citric acid derivatives (e.g. triethyl citrate, tributyl citrate, acetyl triethyl citrate), aliphatic dicarboxylic esters (e.g. dialkyl adipates, sebacic esters, in particular diethyl sebacate, tartaric esters), glycerol monoacetate, glycerol diacetate or glycerol triacetate, fatty acids and derivatives (e.g. glycerol monostearates, acetylated fatty acid glycerides, castor oil and other natural oils, Miglyol), fatty acid alcohols (e.g. cetyl alcohol, cetylstearyl alcohol), sugars, sugar alcohols and sugar derivatives (e.g. erythritol, isomalt, lactitol, mannitol, maltitol, maltodextrin, xylitol). The concentration of plasticizers is normally from 0 to 30%, preferably from 0 to 20% based on the total mass of the gel.

Examples of further suitable water-swellable polymers which may be incorporated in the hydrogel are high-molecular weight polyethylene oxides, xanthan gum, copolymers of vinylpyrrolidone and vinyl acetate, polyvinylpyrrolidones, crospovidones, crosslinked sodium carboxymethylcellulose, crosslinked sodium carboxymethylstarch, low-substituted hydroxypropylmethylcellulose (L-HPC), poly(hydroxyalkyl methacrylate), alginates and galactomannans and mixtures thereof.

The present invention further relates to the combination of formulations with different release properties, e.g. rapid-release and slow-release, in one medicinal form.

As described above, according to one embodiment of the present invention a admix/formulation/mixture which release active ingredients (API) in a controlled fashion over a prolonged period is provided.

If necessary, the pH can be adjusted to 1-8.0 with a buffer composition. The release is carried out at a temperature of 36-42° C.

If necessary, the pH can be adjusted to 1-5.5 with a buffer composition. The release is carried out at a temperature of 36-42° C.

If necessary, the pH can be adjusted to 5.5-9.0 with a buffer composition. The release is carried out at a temperature of 36-42° C.

The amount of active ingredient determined in this way is converted into percent by mass of the amount of active ingredient employed.

The average release rate in the context of the present invention is defined via the time until the release of active ingredient reaches 80%, whereas the initial release describes the percentage release of active ingredient after 30 minutes.

The admix/formulation/mixture according to the invention with controlled release of active ingredient preferably have an average release rate of 80% in the time interval between 3 and 20 hours (80% in 3 hours and 80% in 20 hours).

The admix/formulation/mixture according to the invention with controlled release of active ingredient preferably have an average release rate of 80% in the time interval between 2 and 4 weeks (80% in 2 hours and 80% in 4 weeks).

In a particularly preferred embodiment of the medicament formulations with controlled release of active ingredient of the present invention, the formulation has an average release rate of 80% in the period from 3 and 18 hours and an initial release not exceeding 65% of the active ingredient in the first 30 minutes of release.

The admix/formulation/mixture according to the present invention can be formulated so that a relative low initial release of 0 to 30% in the first 30 minutes or a relative high initial release of 30 to 60% of the medicinal substance in the first 30 minutes of medicinal substance release is achieved.

In a preferred embodiment of the admix/formulation/mixture of the present invention is characterized by an average release rate of 80% in the period from 4 to 18 hours, this has a relatively low initial release of 0 to 25% in the first 30 minutes of release.

Another preferred configuration of the medicament formulations with controlled release of active ingredient has an average release rate of 80% in the period from 3 to 16 hours and is distinguished by a relatively high initial release of 35 to 60% in the first 30 minutes of release of active ingredient.

It should be emphasized that the admix/formulation/mixture with controlled release of active ingredient of this invention refers to all formulations in which the release of active ingredient is modified so that it takes place with a slower delivery rate than from rapid-release medicinal forms such as, for example, a conventional instillation procedure in the case of bladder cancer treatment.

Furthermore, the admix/formulation/mixture with controlled release of active ingredient of the present invention also include formulations with delayed release in which the delivery of the active ingredient is modified so that the release starts at a later time than with a conventional rapid-release medicinal form. The subsequent release from a delayed-release medicinal form may also take place in controlled fashion with a reduced release rate.

The medicament formulations according to the invention may comprise the active ingredient in dissolved, suspended and/or solid, amorphous or crystalline form. The active ingredient can be employed in various particle sizes, e.g. in unground, ground or in micronized form, to produce the admix/formulation/mixture according to the invention with controlled release of active ingredient.

The adhesive and thickening compounds preferably used in the production of coated neutral pellets (e.g. consisting of sucrose, microcrystalline cellulose, citric acid) are polycarbophil (polymer of acrylic acid crosslinked with divinyl glycol), hydroxypropylmethylcellulose (HPMC) and polyvinylpyrrolidone (PVP). It is likewise possible to employ other naturally, synthetic or partially synthetic polymers such as, for example methylcellulose (MC), hydroxy-propylcellulose (HPC), other hydroxyalkylcelluloses and hydroxyalkylmethylcelluloses, carboxy-methylcelluloses and salts thereof, polyacrylic acids, polymethacrylates, gelatin, starch or starch derivatives, as well as gums like guar gum and xanthan gum.

Bonding agents employed for the production of active ingredient-containing microcapsules are for example polycarbophil, cellulose, microcrystalline cellulose, cellulose derivatives such as, for example, HMPC, HPC and low-substituted hydroxypropylcellulose (L-HPC), dicalcium phosphate, lactose, PVP and sucrose, ethylcellulose, hydroxypropymethylcellulose acetate succinate (HPMCAS), PVP, vinylpyrrolidone/vinyl acetate copolymer, polyethylene glycol, polyethylene oxide, polymethacrylates, polyvinyl alcohols (PVA), partially hydrolysed polyvinyl acetate (PVAc), polysaccharides (e.g. alginic acid, alginates, galactomannans) waxes, fats and fatty acid derivatives.

pH-modifying substances such as, for example, acids, bases and buffer substances are incorporated into the active ingredient-containing core. Addition of these substances makes it possible to reduce markedly the pH-dependence of the release of the APIs. Examples of suitable excipients which modify the pH in the active ingredient-containing cores are: adipic acid, malic acid, L-arginine, ascorbic acid, aspartic acid, benzenesulphonic acid, benzoic acid, succinic acid, citric acid, ethanesulphonic acid, 2-hydroxyethanesulphonic acid, fumaric acid, gluconic acid, glucuronic acid, glutamic acid, potassium hydrogen tartrate, maleic acid, malonic acid, methanesulphonic acid, toluenesulphonic acid, trometamol, tartaric acid. Citric acid, succinic acid, tartaric acid, potassium hydrogen tartrate are preferably employed.

Particularly suitable for producing the diffusion coating are ethylcelluloses and polymethacrylates such as, for example, EUDRAGIT® NE, EUDRAGIT® RS and RL. However, other materials such as, for example, cellulose acetate and cellulose acetate butyrate can also be employed as film-forming diffusion-controlling polymers.

Examples of plasticizers used are citric acid derivatives (e.g. triethyl citrate, tributyl citrate, acetyl triethyl citrate), phthalic acid derivatives (e.g. dimethyl phthalate, diethyl phthalate, dibutyl phthalate), benzoic acid and benzoic esters, other aromatic carboxylic esters (e.g. trimellithic esters), aliphatic dicarboxylic esters (e.g. dialkyl adipates, sebacic esters, in particular diethyl sebacate, tartaric esters), glycerol monoacetate, glycerol diacetate or glycerol triacetate, polyols (e.g. glycerol, 1,2-propanediol, polyethylene glycol of varying chain length), fatty acids and derivatives (e.g. glycerol monostearates, acetylated fatty acid glycerides, castor oil and other natural oils, Miglyol) and fatty acid alcohols (e.g. cetyl alcohol, cetylstearyl alcohol). The nature and amount of the plasticizer are chosen so that the above-defined release according to the invention and the necessary stability of the medicinal forms is achieved. The proportion of the plasticizer is from 0 to 50%, preferably 0 to 35%, particularly preferably 0 to 25% based on the mass of the hydrogel composition.

The release rate according to the invention is controlled by the gel composition. Certain components may increase the permeability of the admix/formulation/mixture including water-soluble polymers such as, for example, polyethylene glycols, PVP, PVA, HPMC, HPC, hydroxyethylcelluloses (HEC), MC, carboxymethylcelluloses or their salts, dextrins, maltodextrins, cylcodextrins, dextrans or other soluble substances such as, for example, urea, salts (sodium chloride, potassium chloride, ammonium chloride, etc.), sugars (sucrose, lactose, glucose, fructose, maltose etc.) and sugar alcohols (mannitol, sorbitol, xylitol, lactitol, etc.). Based on the mass of the hydrogel, from 0 to 50%, preferably 0 to 35%, particularly preferably 0 to 20%, increasing permeability components may be employed.

A further aspect of the present invention are coated admix/formulation/mixture which comprise one or more swellable excipients which, on penetration of liquid through the membrane, swell greatly and, through the swelling and volume expansion, cause the coating to split. The splitting of the coating makes it possible for the medicinal substance to be released from the admix/formulation/mixture, usually in pulsatile form. Swellable excipients which these formulations may comprise are, for example, polyvinylpyrrolidones, crospovidones, crosslinked sodium carboxymethylcellulose, crosslinked sodium carboxymethylstarch, polyethylene oxides, polymethyacrylates, low-substituted hydroxypropylmethylcellulose (L-HPC). Examples of suitable coating materials are cellulose acetate, ethylcellulose and polymethacrylates.

The described diffusion-controlled or pulsatile formulations can be employed directly and unmodified as medicinal form. However, they may also be further processed, where appropriate with addition of excipients, to the final admix/formulation/mixture. In order to achieve a desired release profile it is also possible to combine different coated formulations in one medicinal form, and administration of an initial dose can take place for example by combination with rapid-release formulation particles, e.g. uncoated pellets, granules or powder.

In a further embodiment of the admix/formulation/mixture according to the invention with controlled release there is use of formulations which include the active ingredient in a admix/formulation/mixture. These group of admixes/formulations/mixtures release the active ingredient by diffusion and/or erosion.

The mass ratio of active ingredient to the total mass of the admix/formulation/mixture in these novel formulations is in the range from 1:1 to 1:1000, preferably in the range from 1:2 to 1:100.

Admixes/formulations/mixtures which can be employed are water-soluble, water-swellable or water-insoluble substances. The novel formulations preferably comprise one or more water-swellable polymers.

Preference is additionally given to medicinal preparations in the context of this invention which comprise water-soluble, hydrogel-forming polymers, these polymers having a nominal viscosity of at least 0.015 Pa s, preferably at least 0.050 Pa s (measured as 2% strength aqueous solution at 20° C.).

A preferred family of candidates to be utilized as a basis for obtaining said hydrogel is group of tri-block copolymers designated as PEG-PPG-PEG (PEG=Polyethylene glycol and PPG=Polypropylene glycol) and called Poloxamers, that produce reverse thermal gelaton compositions, i.e., with the characteristic that their viscosity increases with increasing temperature up to a point from which viscosity again decreases. In particular, Poloxamer 407 possesses a gelling temperature which is above 10° C. but below the human body temperature, i.e., 37° C. This characteristic may confer the ability of a composition containing the compound to be injected or infused in liquid state into a bodily inner cavity at a low temperature and, afterwards, as the composition warms, it becomes a gel, thus stabilizing upon the wall of the inner human cavity.

This characteristic has allowed PF-127 to be used as a carrier for most routes of administration including oral, topical, intranasal, vaginal, rectal, ocular and parenteral routes. In recent years PF-127 has attracted particular interest in the design of dermal and transdermal delivery systems, with a view to promoting, improving or retarding drug permeation through the skin, bearing in mind that for topical delivery systems, accumulation in the skin with minimal permeation is desired, while for systemic delivery, the opposite behavior is preferred. Poloxamer 407 (PF-127) is a nonionic surfactant composed of polyoxyethylene-polyoxypropylene copolymers in a concentration ranging from 20-30%. At low concentrations ($10^{-4}$-$10^{-5}$%) they form monomolecular micelles, but higher concentrations result in multimolecular aggregates consisting of a hydrophobic central core with their hydrophilic polyoxyethylene chains facing the external medium. Micellization occurs in dilute solutions of block copolymers in selected solvents above the critical micellar concentration, at a given temperature. At higher concentrations, above a critical gel concentration, the micelles can order into a lattice.

In case it may become needed to speed this process of gradual dilution by external actions, in a preferred embodiment, the coating can be removed promptly by cooling the coating below its gelation temperature, thus significantly lowering its viscosity and speeding its dilution into the bladder urine. In a non-limited example, the cooling can be affected by flushing the bladder with a flow of cold liquid such as water or saline through a regular catheter into the bladder. Water and Saline will also help to melt water-based DTCx gels. In another preferred embodiment, the flow of cold liquid can be applied via a special catheter, which will enable a thin or focused jet of liquid that will exert pressure on a small part of the coating. In a preferred embodiment, the direction of this jet may be changed such that it can be activated on several areas of the bladder coating sequentially.

In another preferred embodiment, speeding the removal of the coating can be achieved by applying a chemical agent such as a solvent that can assist in the dissolution of the coating. The chemical agent can be chosen according to the formulation of the DTCx. As a non-limiting example, ethyl or isopropyl alcohol and DMSO (dimethyl suloxide) can be used to dissolve coatings that include lipophilic materials.

The versatility of the polymer composition and the ability to control its physicochemical properties may allow the incorporation and optimaize sustained-release dosing of additional active ingredients that may be desired in a chemotherapy treatment, including the reduction of pain, avoidance of inflammation and other undesired effects. Thus, besides the active ingredients that serve as chemotherapy agents, other drugs can be incorporated in the gel composition, among them anesthetic drugs (e.g., lidocaine), coagulants (e.g., proconvertin) anticoagulants (like heparin), anti-inflammatory drugs (steroidal and non-steroidal) and others, according to the medical requirements for patients suffering of SBC utilizing the effect of gradual release of the diverse active components for an optimal treatment.

According to another embodiment of the present invention, other drugs can be incorporated in the gel composition. Such drugs can be administered topically and can belong to at least one of the following families: Antineoplastic drugs; Chemotherapeutic agents; Anti-infective agents (Antimicrobial drugs, Antiparasitic agents, Antivirals); Drugs acting on the blood and blood forming organs (Antihemorrhagics, Antithrombotic agents, antianemic drugs); Dermatologic drugs (antifungals, antiseptic); Genito-urinary system drugs; Gastrointestinal system (antiobesity, acid related disorders); Metabolism drugs; Anti-inflammatory product; Musculo-skeletal system acting drugs; Neurological drugs; Respiratory drugs; Cardio-vascular drugs; Otological drugs; Anti-infective drugs; Corticosteroids drugs; Analgesics and anesthetics drugs; Antiparasitics drugs or any combination thereof.

According to another embodiment of the present invention, other drugs can be incorporated in the gel composition. Such drugs can be selected from a group consisting of, Antibacterials/Antibiotics, Antiinflammatories/Corticosteroids, Antineoplastics/Cytotoxics, Growth factors such as VEGF (Vascular Endothelial Growth Factor) and Inhibitory factors such as LIF (interleukin 6 class cytokine).

According to another embodiment of the present invention, at least one of the following is utilized in the admix/formulation/mixture: Poly(propylene oxide)—PPO, Poly(lactide-co-glycolic acid)—PLGA, Poly(N-isopropylacrylamide)—PNIPAM, Poly(propylene fumerate)—PPF, Poly(urethane)—PU, Poly(organophosphazene)—POP, Poloxamers of the type PEO-PPO-PEO (Poly(ethylene oxide), Poly(propylene oxide), Poly(ethylene oxide)) such as poloxamer 68, 88, 98, 108, 124, 127, 188, 237, 338 and 407, Stearic Acid, Poly(acrilic acid), Glyceryl Stearate, Cetearyl Alcohol, Sodium Stearoyl Lactylate, Hydroxy-Lenolin or any combination thereof.

According to another embodiment of the present invention the hydrogel\polymer composition may includes active pharmaceutical ingredients (APIs) that are expected to render a better therapeutic performance at lower risk levels. Specifically, the anticancerous drug mitomycin C (MMC) has been experimentally utilized in in vitro settings and applied on the internal bladder wall of animal specimens. The API is released in a controlled manner and the residence time inside the bladder is in the order of up to 24 hours instead of the accustomed 1-2 hours (until micturition).

According to another embodiment of the present invention the admix/formulation/mixture as provided above, can be used as biological glue so as to glue at least two tissues together. By adjusting the viscosity of the admix/formulation/mixture such biological glue can be provided.

It is a further object of this invention to disclose such a method as defined in any of the above, wherein the weight of the balloon filled with a liquid denser than water is used for the application of the gel (utilizing its gravity).

It is a further object of this invention to disclose such a method as defined in any of the above, wherein said step of applying force to said material further comprises a step of filling said catheter balloon with water and positioning the patient to utilize the gravitational forces directly toward the target tissue during the solidification of the material and cause optimal adhesion to that target tissue.

It is a further object of this invention to disclose such a method as defined in any of the above, wherein said step of applying gravitational force to said material further comprises a step of changing the position of the patient before applying partial doses of material to enable substantially full coating of the whole targeted internal cavity surface.

According to another embodiment, the material is used not only for coating internal cavities but rather coating organs selected from urinary bladder, mouth, nasal and paranasal sinus, gallbladder, esophagus, rectum, lungs, vagina, uterus, stomach, renal pelvis, pleura, abdomen, peritoneum, pelvis, liver, kidney, heart, intestine, brain, vertebral column, or any combination thereof.

In order better to illustrate how the invention may be put into practice, the following non-limiting examples of some of the embodiments of the invention are now provided.

Example 1

The effectiveness of the present invention hydrogel composition drug delivery to the urinary tract is demonstrated by the following pre-clinical example. Two embodiments of reverse thermal gelation, mucoandesive and flexible hydrogel mixed with MMC (Kyowa) at a concentration of 1 and 2 mg/ml were prepared as follows.

DTC1: The material comprised Pluronic F-127 Ethylene Oxide/Propylene Oxide Block Copolymer (27.0%); Polyethylene glycol, average MW=400 (PEG-400) (1.0%); Hydroxypropylmethyl cellulose (HPMC) (0.2%); with the remainder water for injection (71.8%) was mixed with MMC (Kyowa) at a concentration of 1 mg/ml.

DTC2: The material comprised Pluronic F-127 Ethylene Oxide/Propylene Oxide Block Copolymer (27.0%); Polyethylene glycol, average MW=400 (PEG-400) (1.0%); Hydroxypropylmethyl cellulose (HPMC) (0.2%); with the remainder water for injection (71.8%) was mixed with MMC (Kyowa) at a concentration of 2 mg/ml.

DTC1 and TDC2 were intravesically instilled in pigs. The MMC concentration in tissue was measured using HPLC and compared to intravesical instillation of 1 mg/ml MMC in water (standard treatment of Non-Muscle Invasive Bladder Cancer; Total MMC dosage of 40 mg). In addition, bladder condition following instillation and in-vivo gel dissolution rate were evaluated. Higher MMC tissue concentrations were obtained following DTC1 and DTC2 hydrogels treatments in comparison to the standard control treatment (MMC in water). Two hours following intravesical treatment of DTC1 the MMC concentration in urithelium tissue was 11 fold higher for the DTC1 in comparison to that of the control treatment (1 mg/ml MMC in water). The MMC concentration following intravesical treatment of DTC2 was 1.8 fold higher than that obtained for TC-3+1 mg/ml MMC. MMC tissue concentration 6 hr following instillation of DTC1 was 13 fold higher than that of the control treatment. Similar average MMC concentrations were obtained for DTC1 and DTC2. No damages to the urothelium contiguity, or bladder wall perforation were observed. The ureters and urethras were intact. No sign of ureter or urethral obstruction was observed. No clinical effects on animal's vital parameter were detected during the complete treatment duration. In addition, residues of MMC hydrogel were observed in the pig bladder 6 hrs following instillation, supporting release duration of more than 6 hr.

Example 2

One embodiment of the material disclosed in the present invention (DTC-1) that incorporates the active therapeutic agent Mitomycin C (MMC) was prepared as follows. The material comprised Pluronic F-127 Ethylene Oxide/Propylene Oxide Block Copolymer (27.0%); Polyethylene glycol, average MW=400 (PEG-400) (1.1%); Hydroxypropylmethyl cellulose (HPMC) (0.2%); MMC (0.1%); with the remainder (71.6%) double distilled water. DTC-1 has an instillation temperature of 30° C.; a sustained release duration of 12 hours; and a degradation time (until fully expelled from the body) of <24 hours.

Example 3

A second embodiment of the material disclosed in the present invention (DTC-1) that incorporates the active therapeutic agent Mitomycin C (MMC) was prepared as follows. The material comprised Pluronic F-127 (27.0%); PEG-400 (1.1%); HPMC (0.2%); MMC (0.2%); with the remainder (71.5%) double distilled water. DTC-2 has an instillation temperature of 50° C.; a sustained release duration of 16 hours; and a degradation time (until fully expelled from the body) of <24 hours.

Example 4

A third embodiment of the material disclosed in the present invention (DTC-3) that incorporates the active therapeutic agent Valrubicin was prepared as follows. The material comprised Pluronic F-127 (27.0%); PEG-400 (1.1%); HPMC (0.3%); Valrubicin (0.1%); with the remainder (71.6%) double distilled water. DTC-3 has an instillation temperature of 50° C.; a sustained release duration of 18 hours; and a degradation time (until fully expelled from the body) of 18 hours.

The increase in the amount of HPMC reduces the release rate from the carrier composition. The dominant release parameter will be the composition dilution in the urine medium. The therapeutic agent is gradually released during the time until the composition is totally expelled from the body.

Example 5

A fourth embodiment of the material disclosed in the present invention (DTC-4), designed to have faster release and expulsion rates and which incorporates the active therapeutic agent MMC, was prepared as follows. The material comprised Pluronic F-127 (27.0%); PEG-400 (1.8%); HPMC (0.2%); MMC (0.1%); with the remainder (70.9%) double distilled water. DTC-4 has an instillation temperature of 30° C.; a sustained release duration of 10 hours; and a degradation time (until fully expelled from the body) of <16 hours.

The decrease in the amount of PEG-400 increases the release rate from the carrier composition and the composition's dilution in the urine medium. In this case, drug is released more rapidly and the composition is totally expelled from the body within 16 hours.

Example 6

A fifth embodiment of the material disclosed in the present invention (DTC-5) that incorporates lidocaine was prepared as follows. The material comprised Pluronic F-127 (27.0%); PEG-400 (1.8%); HPMC (0.2%); Lidocaine 25 mg/10 ml composition (0.25%); with the remainder (70.75%) double distilled water. DTC-5 has an instillation temperature of 60° C.; a sustained release duration of 24 hours; and a degradation time (until fully expelled from the body) of 24 hours.

Example 7

A sixth embodiment of the material disclosed in the present invention (DTC-6) that incorporates the therapeutic agent MMC was prepared as follows. The material comprised Pluronic F-127 (27.0%); PEG-400 (1.1%); HPMC (0.2%); MMC (0.25%); with the remainder (71.35%) double distilled water. DTC-6 has an instillation temperature of 30° C.; a sustained release duration of 18 hours; and a degradation time (until fully expelled from the body) of 24 hours.

Example 8

A seventh embodiment of the material disclosed in the present invention (DTC-7) that incorporates the therapeutic agent Gemcitabine HCl was prepared as follows. The material comprised Pluronic F-127 (25.0%); HPMC (0.2%); Gemcitabine HCl 25 mg/10 ml composition (0.25%); with the remainder (74. %) double distilled water. DTC-7 has an instillation temperature of 20° C.; a sustained release duration of 12 hours; and a degradation time (until fully expelled from the body) of <18 hours.

It should be clarified that the above compositions refer to the use of chemically pure drugs. Commercially, some of the drugs are provided as admixtures of the active ingredient and other non-active compounds. For example, MMC is provided commercially in ampoules that contain 0.1 mg MMC and 240 mg sodium chloride, which provide an isotonic solution when dissolved in 10 ml double distilled water. The presence of salts as sodium chloride in the final material may have a considerable effect in the composition's physicochemical properties, among them and not limited to viscosity and gelation temperature, which are critical in the application method. These filler materials must be considered when formulating the different compositions, which should be adapted to the actual formulation of the active ingredient and its excipients.

Example 9

An in-vitro study was performed to evaluate the efficacy of DTCx materials as cytotoxic agents in the urinary bladder. A carcinoma cell line was treated with MMC incorporated into the material disclosed in the present invention, and the results the treatment were compared to treatment with MMC dissolved in saline. Viability was assessed by MTT assay which tests mitochondrial function.

Cell lines of human bladder cancer were grown in RPMI 1640 medium, supplemented with FBS, 100 U/ml penicillin and 100 mg/ml streptomycin. At Day 1 cells were seeded in 24-well plates at a MMC concentration of $1\times10^4$ (four replicates for each concentration, 1 plate for each analysis time). The cells were then exposed for 24 hours to DTC-2; in separate experiments, DTC-2 samples that contained 0.05, 0.1, 0.5 or 1 μg/ml MMC (Kyowa, Hakko Kogyo Co. Ltd.) were used. After 2 hours of incubation, medium was replaced with fresh medium for all plates.

The plates were tested by taking out the medium and adding fresh medium containing MTT reagent. All other plates were returned to the incubator for incubation of 24, 72, 120 and 144 h. MTT assays were used to assess toxicity at all time points. The proportion of living cells was calculated by comparison to the control vehicle.

A microplate reader (EL 312e: Bio-Tek Instruments, Winooski V T) was used to evaluate the presence of LDH as a color development measured by absorbance spectroscopy at 450 nm. Background optical density (OD) was subtracted from the OD readings of all samples. Cell viability was calculated by dividing the mean OD absorbance values of the treated wells by the mean OD absorbance of the control wells. All samples were tested in triplicate.

Reference is now made to FIG. 3, which shows graphs of cell viability as a function of time for various experiments. These results clearly demonstrate MMC cytotoxicity when different MMC concentrations are used in saline and in TC-2 respectively.

These studies clearly demonstrate that a dramatic effect may be observed in the case of 0.1 μg/ml (see FIG. 3A) where the difference between the effect of the DTC-2 hydrogel and that of the MMC-saline solution is most pronounced. For MMC-saline solution, there is practically no cell-kill, while with DTC-2 the cell-kill effect reaches 60%.

A direct relationship was demonstrated between MMC time of exposure and cytotoxicity. As seen in the graphs, in practically all cases the general trend is that the cytotoxicity increases as exposure time increases.

A direct relationship was also demonstrated between MMC concentration and cytotoxicity. Comparing the graphs obtained for different concentrations shows a higher cytotoxicity effect with the increase of concentration.

Thus, higher concentrations of MMC and longer exposure time contribute significantly to a higher cytotoxicity of MMC. When exposure time was increased from 2 hours to 24 hours, a cell kill level was achieved with less than one third of the MMC dose used for two hours exposure.

MMC concentrations in intravesical instillations have been evaluated in many different studies. Current treatment concentration is the highest that can be tolerated by the patient. Our results demonstrate that a further improvement in MMC efficacy can be gained by increasing the exposure time to MMC even at lower MMC concentrations.

Example 10

The inventors of the present invention conducted a pre-clinical trial with sick female mice model testing the DTCx material (TC-1 polymer and Gemzar chemotherapy) on a MBT-2 disease model. These tumors are extremely aggressive and resistant to chemotherapy therefore somewhat differ from human superficial bladder cancer. In this study, treatment was applied 14, 10, and 3 days following cell implantation. Each group was divided into a DTCx material arm and a standard instillation arm consisting of Gemzar in saline, which served as control group. The results showed that the procedure was safe (indeed, with low mortality) and efficient, that is, consistent lower weights of cancerous bladder in the DTCx arm were obtained as compared to the control arm.

Large animal safety and efficacy studies were conducted on female pigs. The results demonstrated excellent control and no catheter-related or method-related adverse events.

The safety of the present invention's material and procedure by comparing the outcome of one week follow-up of animals following DTC-2 instillation to standard MMC instillation—seeking short & medium term adverse events (urinary retention, urethral obstruction, toxicity—both local and systemic).

Comparison of MMC concentrations in bladder tissue at 12 hours following instillation versus standard 2-hour instillation has demonstrated significantly higher MMC concentration in the bladder tissue for the procedure of the present invention, demonstrating the improved efficacy of the material and method disclosed in the present invention relative to methods known in the art for applying MMC to bladder tissue.

Example 11

Studies performed by the inventors demonstrate that controlled release of the drug can be obtained which considerably prolong the actual contact between the bladder wall and the drug. This slow-release effect, which can take between 16 and 24 hours, dramatically increases such contact time and thus the continuous therapeutic effect of the drug upon the cancerous tissue. This effect, in tandem with the creation of an effective, stable coating upon the bladder wall, is expected to render a superior therapeutic effect in the treatment of bladder cancer.

In vitro studies performed by the inventors showed a gradual release of the drug embedded in the polymer composition in conditions similar to those of a human bladder (37° C., urine medium). The drug was gradually released throughout the tests over the course of 12-24 hours.

Further in vitro studies performed by the inventors show a gradual release of the drug embedded in the polymer composition in conditions similar to those of a human bladder (37° C., urine medium) when instead of continuously exposing the polymer composition to one portion of urine, such urine is changed every two hours and fresh portions replace the older ones during 24 hours. It was again found that the drug was gradually released throughout the tests during 16-24 hours.

A parallel set of in-vitro release experiments were performed using membraneless dissolution model: The hydrogel was loaded with the tested drug, layered in a glass containers, and equilibrated in the experimental temperature until homogenous gel layer was formed. acceptor solution was discarded every hour and replaced by a fresh solution. Drug concentration in acceptor solution was measured spectrophotometrically, gel dissolution was determined gravimetrically. Two examples are provided here.

a. Reverse thermal gelation hydrogel composed of Pluronic F-127 Ethylene Oxide/Propylene Oxide Block Copolymer (27.0%); Polyethylene glycol, average MW=400 (PEG-400) (1.0%); Hydroxypropylmethyl cellulose (HPMC) (0.2%); and the remainder water for injection (71.8%) was loaded with at a concentration of 10 mg/ml and 20 mg/ml Lidocaine hydrochloride.

Figure 7:
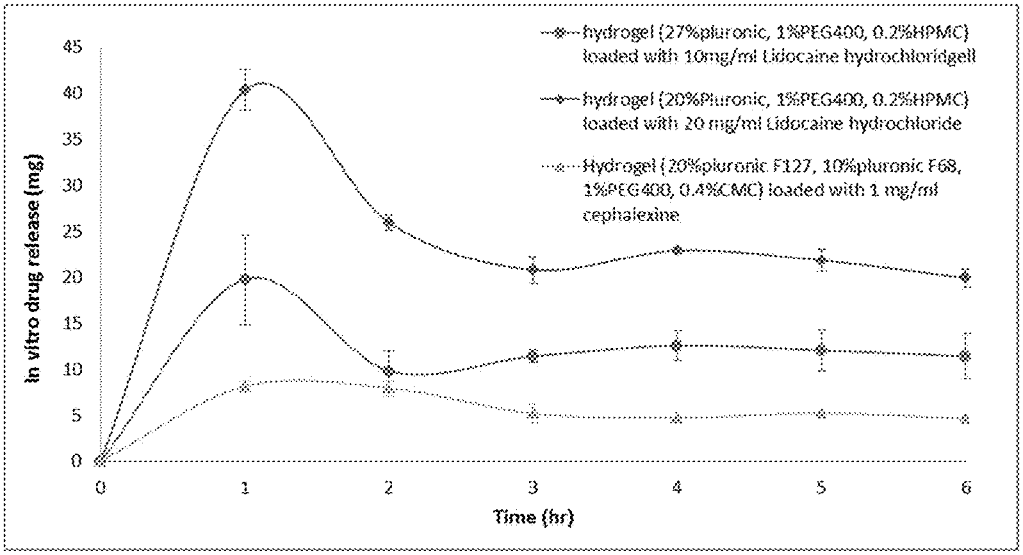
FIG. 7 presents results of measurements of in vitro release of Lidocaine hydrochloride (10 and 20 mg/ml) from reverse thermal hydrogel (including 27% Ethylene Oxide/Propylene Oxide Block Copolymer, 1% PEG-400, 0.2% Hydroxypropylmethyl cellulose in water) and Cephalexin (1 mg/ml) from reverse thermal hydrogel (20.0% Pluronic F-127, 10% Pluronic F-68 (10.0%) 1.0% PEG-400 0.4% CMC sodium in water; and, FIG. 8 shows results for the dissolution rate of hydrogels according to several different embodiments of the invention.

The in vitro release of Lidocaine hydrochloride (10 and 20 mg/ml) from the hydrogel formulation enclosed above is shown in FIG. 7. The released amount of Lidocaine hydrochloride was twofold higher for hydrogel loaded with 20 mg/ml Lidocaine hydrochloride in comparison to the hydrogel loaded with 10 mg/ml Lidocaine hydrochloride formulation. In addition, higher amount of Lidocaine hydrochloride was released from both formulations to the acceptor solution in the first testing time point (1 hr). The amount of Lidocaine hydrochloride released in the following time points was relatively constant.

b. Reverse thermal gelation hydrogel composed of Pluronic F-127 (20.0%); Pluronic F-68 (10.0%) Polyethylene glycol, average MW=400 (PEG-400) (1.0%); carboxymethyl cellulose soidium (CMC) (0.4%); and the remainder water for injection (68.8%) was loaded with at a concentration of 1 mg/ml cephalexin.

The in vitro release of cephalexin (1 mg/ml) from the hydrogel formulation enclosed above is shown in FIG. 7. The results demonstrate constant release of cephalexin at 3-6 hrs.

Example 12

Studies were performed on the adhesiveness of the material of the present invention to mucosal tissue. Remarkable, unexpected results were obtained.

Adhesiveness was measured by the "rolling ball" method according to the ASTM D-3121-94 and PTSC-6 standard methods. In these experiments, the adhesiveness of the material disclosed in the present invention was compared to the adhesiveness of compositions disclosed in U.S. Pat. Nos. 6,207,180; 6,894,071; and U.S. Pat. Appl. US2006/0127210. The results indicate that the material is potentially suitable for use as a drug carrier for the treatment of bladder cancer. The results are summarized in Table 2 and show a difference of at least 20 times in adhesive power.

TABLE 2

| Composition | Test 1 Result (cm) | Test 2 result (cm) |
|---|---|---|
| U.S. Pat. No. 6,207,180 | 32 | 20 |
| U.S. Pat. No. 6,894,017 | >45 | >28 |
| U.S. Pat. Appl. 2006/0127420 | >45 | >28 |
| present invention | 1.0 | 1.6 |

Example 13

A second comparative study was performed in which the adhesiveness of the material of the present invention to biological material was compared with those of the three compositions cited in the previous example. The tests were performed according to ASTM standard D-2256-03, which determines adhesiveness by measuring peel strength. Adhesive properties were assessed applying equal amounts of the four compositions to biological tissues. Different types of loads were subjected to the samples, in order to mimic conditions occurring during in vivo applications. To standardize the test results, with respect to the multiplicity of applications and of tissues treated, pig bladder tissue was used as the unique substrate. The results are summarized in Table 3.

TABLE 3

| Composition | Adhesiveness ($N/cm^2$) |
|---|---|
| U.S. Pat. No. 6,207,180 | 0.068 |
| U.S. Pat. No. 6,894,017 | 0.047 |
| U.S. Pat. Appl. 2006/0127420 | 0.090 |
| present invention | 1.77 |

These results demonstrate that the material of the present invention is at least 20 times more adhesive to biological tissue than the materials known in the prior art.

Example 14

A second set of in vitro tests of the bioadhesive properties of the material disclosed herein was performed. These tests were performed on fresh female swine bladder using a TAXT2 texture analyzer according to the following protocol.

A tissue specimen was placed on a foam tape mounted onto the cylindrical support of the instrument (2 cm diameter and 4 cm length) and secured with a string. The whole support was then positioned at the top of the measuring system and held in place by a clamp. A given weight of hydrogel (for example, 0.5 g) was evenly poured onto another support of similar dimensions. The support was then affixed on the lower probe of the instrument. The two supports were aligned to ensure that the gel comes into direct contact with the surface of the swine tissue when the upper support is lowered. Measurements were performed at 25° C.

Before measurement, 100 μl of simulated urine fluid was evenly spread on the surface of the tissue. The upper support was then lowered at a speed of 0.5 mm/s to contact with the gel at a force of 1 N for a contact time of 10 s. It was then withdrawn at a rate of 1.0 mm/s to a distance of 10 mm. An acquisition rate of 200 points/s was chosen for the analysis. Data collection and calculation can be performed using the XTRA Dimension software package of the instrument. The work of adhesion and peak detachment force were used to evaluate the bioadhesive strength of the films. The work of adhesion is calculated from the area under the force-distance curve, and the peak detachment force is taken as the maximum force needed for detaching the film from the tissue. All measurements were performed in triplicate. The results are summarized in Table 4.

TABLE 4

| Formulation | Pluronic F127 | HPMC | PEG 400 | Double Distilled Water | Work of Adhesion (mJ) | Peak Detachment Force (N) |
|---|---|---|---|---|---|---|
| A | 25.0% | 0.1% | 0.5% | balance | 0.51 | 3.34 |
| B | 27.0% | 0.1% | 1.0% | " | 0.73 | 4.43 |
| C | 27.0% | 0.2% | 1.0% | " | 1.13 | 6.35 |

A marked increase in the bioadhesion strength was observed with an increase in HPMC content.

Example 15

Gel point measurements were made for a number of embodiments of the material herein disclosed. The general procedure for the measurements was as follows. First, 50 ml of the material was poured into a 100-ml glass container. A TEFLON-coated magnet of 2-2.5 cm length was then placed in the container. A thermocouple was then inserted into the bulk of the hydrogel. The container was placed in an ice bath on a magnetic stirrer plate. After the temperature of hydrogel dropped to 5° C., the ice bath was removed from the magnetic stirrer and the glass container containing the hydrogel was placed directly on top of the magnetic stirrer plate. The magnetic stirrer was then turned on and run at medium speed (120 rpm). The temperature was allowed to rise gradually (~1° C./min) to room temperature. The gel point for a particular measurement was recorded as the temperature at which the magnet stopped rotating. For each sample, the entire procedure was performed twice, and the gel point determined as the average of the two measurements.

The gel point was measured for three different embodiments of the material disclosed herein. The results of the measurements are summarized in Table 5.

TABLE 5

| Formulation | Pluronic F127 | HPMC | PEG 400 | Double Distilled Water | Gel Point (° C.) |
|---|---|---|---|---|---|
| A | 25.0% | 0.1% | 0.5% | balance | 16.5 |
| B | 27.0% | 0.1% | 1.0% | " | 14.1 |
| C | 27.0% | 0.2% | 1.0% | " | 11.9 |

A further set of tests was performed in which MMC was incorporated into the material at a typical dosage concentration in order to determine the effect of the MMC (and its accompanying excipient) on the gel point of the final composition. Formulation D includes pure MMC; formulation E includes commercially obtainable MMC that includes 2 parts mannitol per 1 part MMC (for example, Boehringer Mannheim) and Formulation F includes 24 parts of sodium chloride per 1 part MMC (for example, Kyowa). The results are summarized in Table 6.

TABLE 6

| Formulation | Pluronic F127 | HPMC | PEG 400 | MMC | NaCl | Mannitol | Double Distilled Water | Gel Point (° C.) |
|---|---|---|---|---|---|---|---|---|
| D | 27.0% | 0.2% | 1.0% | 0.1% | 0 | 0 | balance | 11.8 |
| E | 27.0% | 0.2% | 1.0% | 0.1% | 0 | 0.2% | " | 11.5 |
| F | 27.0% | 0.2% | 1.0% | 0.1% | 2.4% | 0 | " | 5.1 |

As can be seen, incorporation of NaCl into the commercial MMC significantly lowers the gel point while mannitol does not affect the gel point very much. The major drop in gel point produced by NaCl as compared to that of mannitol can be explained by (a) the fact that the concentration of NaCl is significantly larger and (b) NaCl is an inorganic salt, thus releasing a number of moles of ions that is twice the number of moles of the original NaCl. The drop in gel point due to the addition of MMC itself is insignificant for practical purposes.

In addition to the gelation point of the reverse thermal gelation hydrogel its viscosity as a function of temperature is an important feature that determines the hydrogel's behavior and ability to perform properly. Therefore the rheological properties of formulation candidates were studied. The viscosity vs temperature curves and values of Tg (gelling temperature) for each formulation were determined by RV DV III Brookfield rheometer and DVII LV viscometer. The temperature at which a sharp increase in viscosity was obtained was determined as Tg. The viscosity measurement of the solid state of the gel (after complete solidification) was out of the range of the used rheometer and viscometer.

Reference is now made to FIG. 5, which presents a semi-logarithmic graph of viscosity as a function of temperature over a range of 5-35° C. for six different embodiments of reverse thermal hydrogels disclosed in the present invention composition for effective drug delivery (TCA, TCB, TCC, TCD, TCE, TCF), and Table 7, which presents the results of a sample gel point measurements.

TABLE 7

| Formulation | Pluronic F127 | Pluronic F68 | HPMC | CMC | PEG-400 | Gel Point |
|---|---|---|---|---|---|---|
| TCA | 27.0% | — | 0.2% | — | 1.0% | 15° C. |
| TCB | 20.0% | — | 0.2% | — | 1.0% | 22° C. |
| TCC | 20.0% | 10.0% | 0.2% | — | 1.0% | 33° C. |
| TCD | 25.0% | 5.0% | 0.2 | | 1.0% | 17° C. |
| TCE | 20.0% | 10.0% | — | 0.4% | 1.0% | |
| TCF | 20.0% | — | — | 0.2% | 1.0% | 20° C. |

This information is fundamentally important for the design and engineering of the hydrogel device since viscosity characteristics are critical in the gel flow through the catheter and spreading upon the bladder inner surface as it is injected by means of the catheter.

Example 16

One of the main features that determines the hydrogel's behavior and ability to perform properly is its viscosity as a function of temperature. Therefore the rheological properties of formulation candidates were studied, including viscosity as a function of temperature and determination of gelling temperature (Tg).

The viscosity vs temperature curves and values of Tg (gelling temperature) for each formulation were determined by means of an AR 1000-N Rheolyst rheometer (TA Instruments). The determination of Tg was determined through the crossover of the G' (elastic modulus) and G" (viscous modulus) curves (see graph below the curves for TC-A).

Figure 5A:
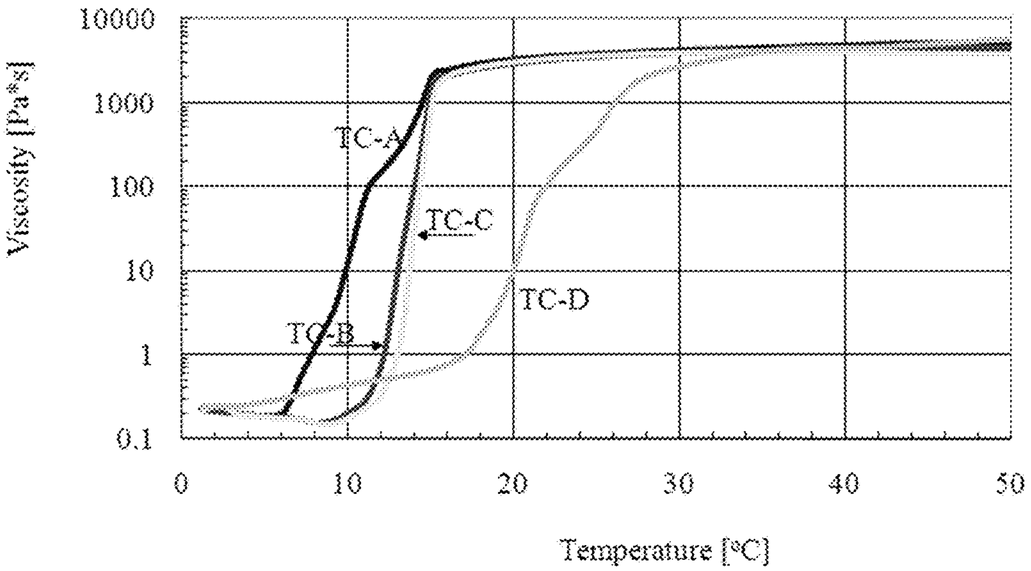
FIG. 5A presents a semi-logarithmic graph of viscosity as a function of temperature for four different embodiments of the material herein disclosed (TC-A, TC-B, TC-C, TC-D)
Figure 5B:
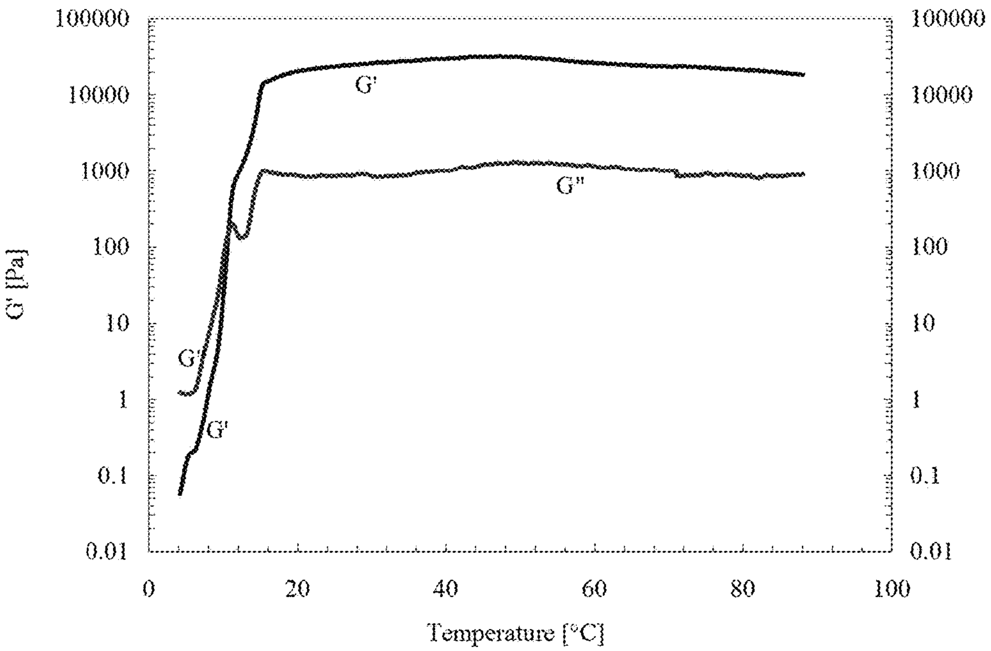
FIG. 5B presents the results of sample gel point measurements.

Reference is now made to FIG. 5A, which presents a semi-logarithmic graph of viscosity as a function of temperature over a range of 4-50° C. for four different embodiments of the material herein disclosed (TCA, TCB, TCC, TCD), and to FIG. 5B, which presents the results of a sample gel point measurements. The formulations of the four embodiments are summarized in Table 8.

TABLE 8

| Formulation | Pluronic F127 | HPMC | PEG-400 | Gel Point |
|---|---|---|---|---|
| TCA | 27.0% | 0.2% | 1.0% | 11.9° C. |
| TCB | 25.5% | 0.2% | 1.0% | 14.5° C. |
| TCC | 25.5% | 0.15% | 1.0% | 14.8° C. |
| TCD | 23.0% | 0.15% | 0.5% | 22.3° C. |

Interestingly, increase in viscosity with temperature in the low temperature range is approximately logarithmic. As can be seen in the graph, even minor modifications of the same basic formulation can produce substantial changes in the rheological behavior of the product.

For TC-A, the values of viscosity in the temperature range of interest are 16 Pa s at 10° C., which is the temperature at which the gel (which at that temperature is still in liquid form) is expected to be cooled before application upon the bladder wall; and 4,600 Pa s at 37° C., which is the gel's final temperature (body temperature). As explained below, the method utilized allowed the determination of the gel point as well.

This information is fundamentally important for the design and engineering of the catheter/hydrogel device since viscosity characteristics are critical in the gel flow through the catheter and spreading upon the bladder inner surface as it is injected by means of the catheter.

Example 17

According to another embodiment, the mixture of gels obtained, according to the present invention, adhere well to the inner surface of human cavities, by their inherent reverse thermal gelling properties. Furthermore, they release the drug in a controlled way and that they themselves (the gels) gradually degrade so that they are expelled from the body in up to 24 hrs.

The following are further examples of mixtures according to the present invention:

17.1—Vitamin gel for topical action provided, according to the following:

| | |
|---|---|
| Vitamin (A, D or K) 0.05% w/w Lecithin | 12% |
| PEG 800 | 1% |
| Isopropyl stearate | 8% |
| Pluronic F-127 | 20% |
| Double distilled water (DDW) | to 100% |

17.2—Paclitaxel gel for cancer treatment, according to the following:

| | |
|---|---|
| Paclitaxel | 0.1% |
| Pluronic F-127 | 10.0% |
| Isopropyl Palmitate | 1.0% s |
| Lecithin | 0.8% |
| Sodium Acryloyldimethyl - Taurate Copolymer | 1.2% |
| Sorbic Acid | 1.0% |
| Potassium Sorbate | 0.1% |
| DDW | to 100% |

17.3—Oral anesthetic gel, according to the following:

| | |
|---|---|
| Lidocaine | 1.0% |
| Pluronic F-127 | 27% |
| Ethoxyl diglycol | 10% |
| Lecithin | 2.0% |
| Mint flavor | 0.1% |
| DDW | to 100% |

17.4—Anti-inflammatory composition, according to the following:

| | |
|---|---|
| PEG-PLGA-PEG* | 24.5% |
| HPMC | 0.2% |
| PEG 400 | 0.5% |
| Ibuprofen | 0.2% |
| DDW | to 100% |

*Ethylene glycol-lactic acid-co-glycolic acid-ethylene glycol triblock copolymer 17.5—Antibacterial gel, according to the following:

-continued

| | |
|---|---|
| PEG 400 | 1.5% |
| PEG 1200 | 12.0% |
| Polysorbate 60 | 6% |
| Pluronic F-127 | 22% |
| Polyvinyl pirrolidone - iodine complex | 5.5% |
| DDW | to 100% |

17.6—MMC gel, according to the following

| | |
|---|---|
| Pluronic F-127 | 20% |
| Carboxymethyl cellulose sodium | 0.5% |
| PEG 400 | 1% |
| MMC | 0.2% |
| In 50 mM Tris-HCL buffer pH = 8 | to 100% |

17.7—Botox gel, according to the following

| | |
|---|---|
| Pluronic F-127 | 20% |
| Carboxymethyl cellulose sodium | 0.4% |
| PEG 400 | 1% |
| Botox | 5 U/gr |
| In 50 mM buffer acetate pH = 5 | to 100% |

Example 18

The effect of PEG-400 concentration on the gelation temperature was tested. The gelation temperature was determined at the temperature at which a sharp increase in the viscosity was observed (viscosity at gelation>$10^6$ mPa s) in a Brookfield rheometer spindle 52. The results are summarized in Table 9.

TABLE 9

| Formulation | HPMC | PEG-400 | Pluronic F127 | Gelation temperature (° C.) |
|---|---|---|---|---|
| a | 0.2 | 1 | 27 | 15 |
| b | 0.2 | 10 | 27 | 6 |

Example 19

The effect of HPMC concentration on the gel viscosity was measured. Viscosity measurements were performed using a Brookfield rheometer DV-III, spindle 52, at 6° C., and represent the viscosity of the formulation in its liquid state. The results are summarized in Table 10.

TABLE 10

| Formulation | HPMC (% w/w) | PEG-400 (% w/w) | Pluronic F127 (% w/w) | Viscosity (mPa s) |
|---|---|---|---|---|
| 1 | 0.2 | 1 | 27 | 223 |
| 2 | 0.5 | 1 | 27 | 357 |
| 3 | 1.5 | 1 | 27 | 603 |
| 4 | 0.2 | 1 | 20 | 96 |
| 5 | 0.5 | 1 | 20 | 431 |
| 6 | 1.5 | 1 | 20 | 5742 |

Example 20

Figure 6:
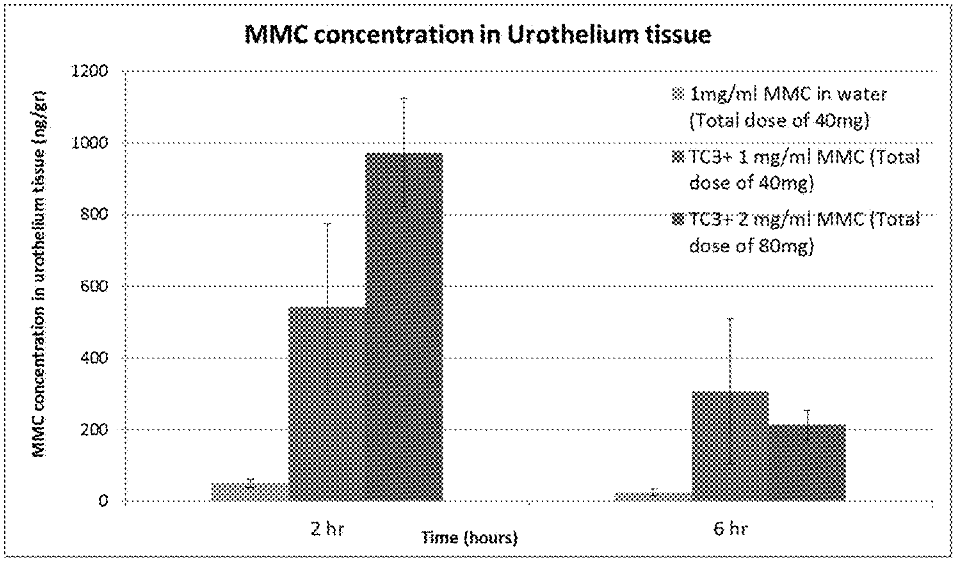
FIG. 6 presents a graph showing the delivery of MMC to pig bladder tissue by use of a gel according to one embodiment of the present invention.

A gel composition according to the present invention was used for delivery of Mitomycin C (MMC) to pig bladder. MMC was incorporated into a gel containing 0.2% (w/w) HPMC, 1% (w/w) PEG-400, 27% (w/w) Pluronic F127 in water. In one experiment, the MMC concentration in the gel was 1 mg/ml (total dosage 40 mg); in another, the MMC concentration was 2 mg/ml (total dosage 80 mg). In each case, as a control, MMC was delivered from a solution containing MMC in the same concentration as in the analogous gel. The experimental results are summarized in FIG. 6.

As can be seen in the figure, higher MMC tissue concentrations were obtained following application of MMC contained in a gel of the present invention than by using a solution of MMC. Two hours following intravesical treatment by gel containing 1 mg/ml MMC, the MMC concentration in the tissue was 11 times higher than in the control. The MMC concentration in the tissue following application of gel with 2 mg/ml was 1.8 times higher than that in the experiment in which the concentration was 1 mg/ml. Six hours following treatment by gel containing 2 mg/ml MMC, the tissue MMC concentration was 13 times higher than in the control.

Example 21

An additional example for the effective drug delivery to the urinary tract of the present invention composition was demonstrated by a preclinical study testing the delivery of botullinium toxin A (BoNT-A) to rats bladder induced with chronic cystitis.

The effect of BoNT-A mixed with one embodiment of the invented material DTC-4 on bladder cystitis was demonstrated in a rat model (Sprague-Dawley) by comparing the effect of intravesical administration of BoNT-A in saline and in gel. The BoNT-A gel formulation (DTC-4) tested included 20 U BoNT-A/ml gel composed of 27% Pluronic F127, 0.2% HPMC and 1% PEG-400 in water. Intravesical instillation of just DTC-4 and of saline with no botullinium toxin served as control groups. Chronic cystitis was induced by intraperitoneal injection of Cyclophosphamide (75 mg/kg was injected on day 1, 4 and 7). On day 2 PE-50 tubing was inserted into the rat bladder through the urethra. The bladder was emptied of urine and filled with DTC-4 or saline with and without BoNT-A (1 ml, 20 u/ml Allergan). On day 8 the animals were anesthetized and their bladders were examined by cystometrogram recording via PE-50 tube inserted into the bladder dome. After recovery the animals were gently restrained and the suprapubic catheter was connected to infusion pump (0.08 ml/min continuously) and pressure transducer for recording intravesical pressure and for saline infusion into the bladder to elicit repetitive voiding. The amplitude and the inter-contraction interval of reflex bladder contractions were recorded. Each tested groups included 2-4 rats.

Figure 4A:
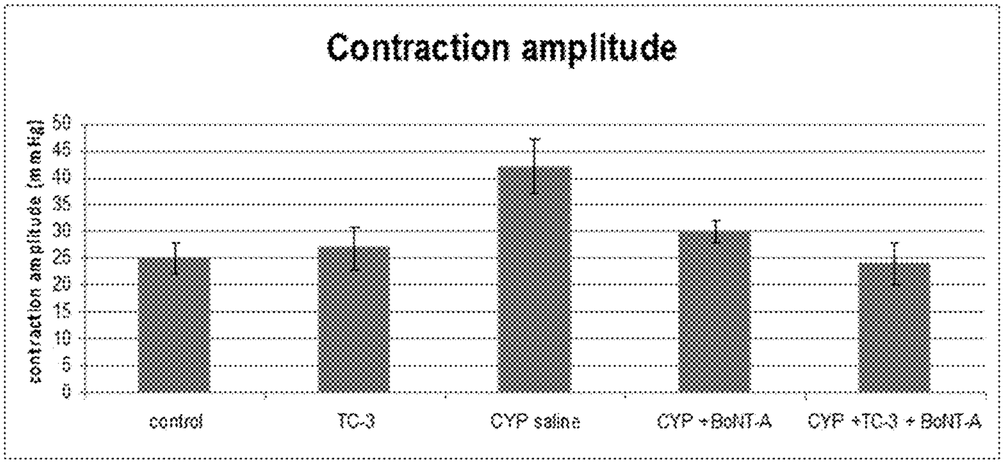
FIG. 4 presents graphically the results of a study of the effect of botulinum toxin gel on contraction of animal bladder as model for overactive bladder contraction; contraction amplitude (FIG. 4A) and inter contraction interval (FIG. 4B) are shown.
Figure 4B:
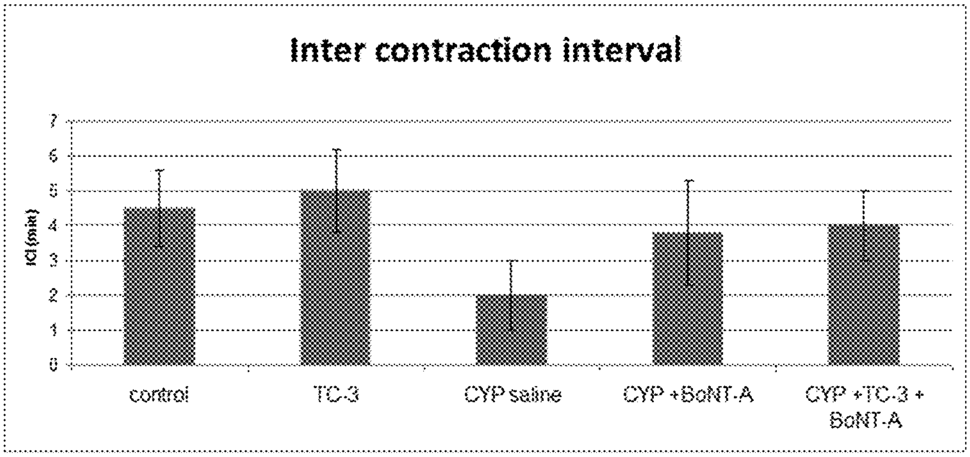

The bladder contraction amplitude measured is shown in FIG. 4. The results demonstrate that following CYP administration the bladder contraction amplitude increased from 25-27 mmHg (contraction level for rat bladder with no hyperactivity) to about 42 mmHg. Following administration of BoNT-A in saline and in TC-3 gel to rats with induced chronic cystitis the contraction decreased to the baseline level amplitude of 30 mmHg and 24 mmHg, respectively. Better response was received for the BoNT-A in gel treatment demonstrating the activity of the BoNT-A in gel and efficacy of BoNT-A mixes with gel treatment.

Similar results were obtained for the measurements of bladder inter-contraction intervals summarized in FIG. 4. Following CYP administration the bladder inter-contraction intervals were shown to decrease from 4-5 min for rat administered with saline or gel to 2 min. Intravesical administration of BoNT-A in saline and in TC-3 gel to rats with induced chronic cystitis increased the inter-contraction intervals to about 4 min, close to the inter-contraction intervals for bladder with no hyperactivity. These results further support the activity of the BoNT-A in the gel and the efficacy of the BoNT-A mixes with gel treatment.

Example 22

In order for the hydrogel formulation to be suitable for drug delivery in the bladder it must comply with the natural physiological changes in volume and shape i.e expansion during urine accumulation and contraction during urine voiding. During its the physiological function the bladder expends to about 5 times its original size. This property is tested for each hydrogel composition in the manner described hereof:

The flexibility of one embodiment of the reverse thermal gelation hydrogel (DTC1) for drug delivery was tested in vitro using sheep bladder tissue. To investigate the effect of tissue tension/expansion on hydrogel coverage, DTC1 stained with methylene blue was layered on top of a the mucosal side of rectangle section of bladder tissue with an area of 3*3 cm. Following hydrogel gelation the tissue was starched and expanded by 3 fold to each direction (horizontally and vertically). The received area was 9 fold larger than the initial surface tissue area. The hydrogel coverage of the tissue following tissue expansion was examined. The hydrogel was shown to follow the stretched tissue. No gel detachment was observed.

Example 23

An important feature that influences the hydrogel is its dissolution rate/erosion rate. Therefore dissolution properties of hydrogels disclosed in the present invention composition were studied.

The dissolution rate was determined using an in-vitro membrane free dissolution model at 37° C. In this model the gel is dissolved into the receptor medium (Dulbecco's phosphate buffer saline) which is carefully layered on top of a smooth and flat gel layer. The amount of gel dissolved is determined gravimetrically. After each sampling of the receptor medium it is carefully discarded and replaced by a fresh medium.

Figure 8:
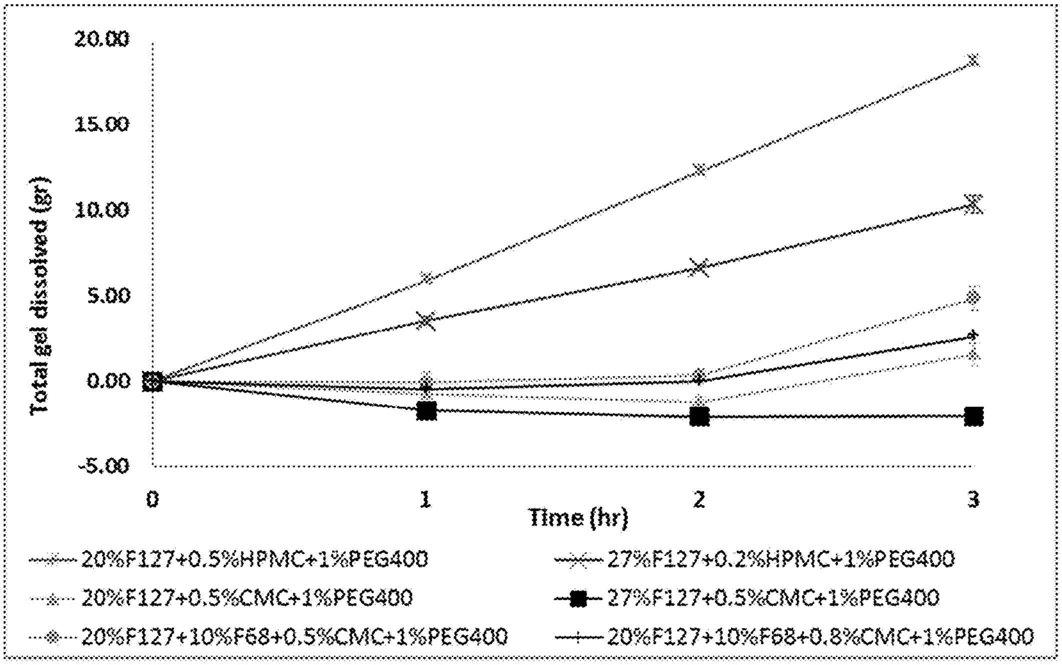

Reference is now made to FIG. 8, which presents the dissolution rate of six different hydrogels herein disclosed. The results demonstrate different dissolution rate of the various formulations tested. These various dissolution rates will determine the treatment duration following instillation of the drug loaded hydrogel. Hence, the reverse thermal gelation hydrogel composition for effective treatment of the urinary tract will be set based on the beneficial treatment duration for specific disease.

Example 24

A further embodiment of the material disclosed in the present invention (DTC-11) is utilized upon organ linings consisting of serous tissue that does not possess a mucosal layer, in particular pleural and peritoneal walls. A condition common in several lung and heart diseases is pleural effusion, when serous fluids, pus or chyle accumulate into the space between the visceral pleura and the parietal pleura layers surrounding the lungs—condition called also hydrothorax. Certain malignancies enlarge the space between pleura layers and cause excessive levels of fluids to accumulate and impair breathing. Standard treatments for pleural effusions is the insertion of intercostals drain, often accompanied by surgical pleurodesis—in which the two pleural surfaces are scarred to each other so that no fluid can accumulate between them. Surgical joining of the layers is not always successful, but it is permanent.

A material of the present invention can be administered into the pleura cavity to adhere to the pleura layers and provide both a mechanical bond and sustained release of drug for treatment of the underlying malignancy (e.g. Tetracycline antibiotic for bacterial infection, or NSAID such as Naproxen to treat fever and inflammation).

The pleura-hydrogel material is inserted into the pleura space via a catheter or trocar, as non-viscous liquid at a temperature that is below 20° C. and adheres to the surrounding tissue as it heats to body temperature. The material is designed to dissolve gradually into the pleura fluids over less than a week and both maintain mechanical support and release therapeutic agents during that whole period.

This procedure can replace the more invasive pleurodesis with the additional benefits of tissue damage reduction, the soothing effect of the hydrogel and improved healing due to the sustained release of anti-inflammatory agents.

The following exemplary formulation can be applied (DTC11):

| | |
|---|---|
| PEG-PLGA-PEG* | 24.5% |
| HPMC | 0.1% |
| PEG 400 | 0.4% |
| DDW | to 100% |

*Ethylene glycol-lactic acid-co-glycolic acid-ethylene glycol triblock copolymer Said composition adheres well to said walls providing an effective matrix for the transport and release of therapeutic active ingredients. In particular, the admixture can carry anti-inflammatory drugs to be applied in case of pleural or peritoneal inflammation.

Example 25

Fixation of organs and prevention of tissue adhesion in the abdomen during laparoscopy:

A material of the current invention can be introduced into the abdomen cavity and provide mechanical support to the target organs in the position that best fits the surgical procedure. The peritoneum-hydrogel material can be inserted into the peritoneum cavity via endoscope working channel, a catheter or trocar, as non-viscous liquid at a temperature that is below 15° C. and adhere to the surrounding tissue as it heats to body temperature. The material is designed to dissolve gradually into the pleura fluids over less than a week and both maintain mechanical support of the organs for several hours and release the drugs during a longer period.

Similar method, but with different materials can be used to prevent the adhesion of tissues between organs in the treated area, which may often occur during laparoscopic surgery.

The main advantages of this method are the combination of its ability to replace a more invasive procedure, the reduction of tissue damage, the soothing effect of the hydrogel and the enhanced healing effect of the sustained release of anti-inflammatory agents. A further advantage is the prevention of the need to remove the fixation surgically because of the natural degradation and expelling of the invented material from the treated area.

The following exemplary formulation can be applied (DTC-12):

| | |
|---|---|
| PEG-PLGA-PEG* | 24.5% |
| CMC | 0.4% |
| PEG 400 | 0.4% |
| DDW | to 100% |

Example 26

A binary API system (DTC-13 to DTC-16) was formulated which allowed a different release profile from the same gel structure. The relative release rate from the basic formulation was controlled by the addition of changing amounts of the surfactant sodium dodecyl sulfate (SDS), which affected the overall lipophilic/hydrophilic balance of the formulation. The APIs in question were mitomycin C (MMC) and lidocaine. The following table presents the composition of three basic formulations and the release time of 80% of each of the two APIs. From an applicative point of view, it is of much interest to obtain a relatively rapid release of lidocaine, which produces the local anesthetic effect upon the organ tissue to be treated, followed by a slow release of the MMC, that may allow a superior chemotherapeutic treatment of said organ.

TABLE 11

| MATERIAL | DTC-13 | DTC-14 | DTC-15 | DTC-16 |
|---|---|---|---|---|
| Pluronic F127 (%) | 27.0 | 27.0 | 27.0 | 27.0 |
| HPMC (%) | 0.2 | 0.2 | 0.2 | 0.2 |
| PEG-400 (%) | 1.0 | 1.0 | 1.0 | 1.0 |
| SDS (%) | 0 | 0.05 | 0.1 | 0.2 |
| DDW (%) | 71.8 | 71.75 | 71.7 | 71.6 |
| MMC (%) | 0.1 | 0.1 | 0.1 | 0.1 |
| Lidocaine (%) | 1.0 | 1.0 | 1.0 | 1.0 |
| Release time 80% MMC (hrs) | 16 | 15 | 14 | 12 |
| Release time 80% Lidocaine (min) | 180 | 120 | 60 | 10 |

The results shown in table 11 demonstrate that adding a small amount of SDS dramatically affects the release profile of the two drugs respectively. This exemplifies, without limiting, the possibilities of engineering the gel composition in a way that allows two or more different APIs to release from the gel matrix each at their own pace—according to the treatment needs. In the example above, it may be desirable, for example, that the soothing effect of the lidocaine be felt by the patient rapidly, just before the MMC commences its own activity, that may be painful, and thus a rapid release of the lidocaine may be desired while a slow release of the same may be unfelt and this ineffective. On the other hand, one can conceive other treatments where a lower but more prolonged anesthetic effect be required, and thus the formulation will change accordingly. The possibilities are limitless as presented by the non-limiting examples above.

Example 26

Prior to testing the efficacy of botulinum toxin (BTX) incorporated into Gel A as a treatment for bladder disorders characterized by bladder spasms, the activity of BTX in the gel and following release from the gel was confirmed.

Figure 9:
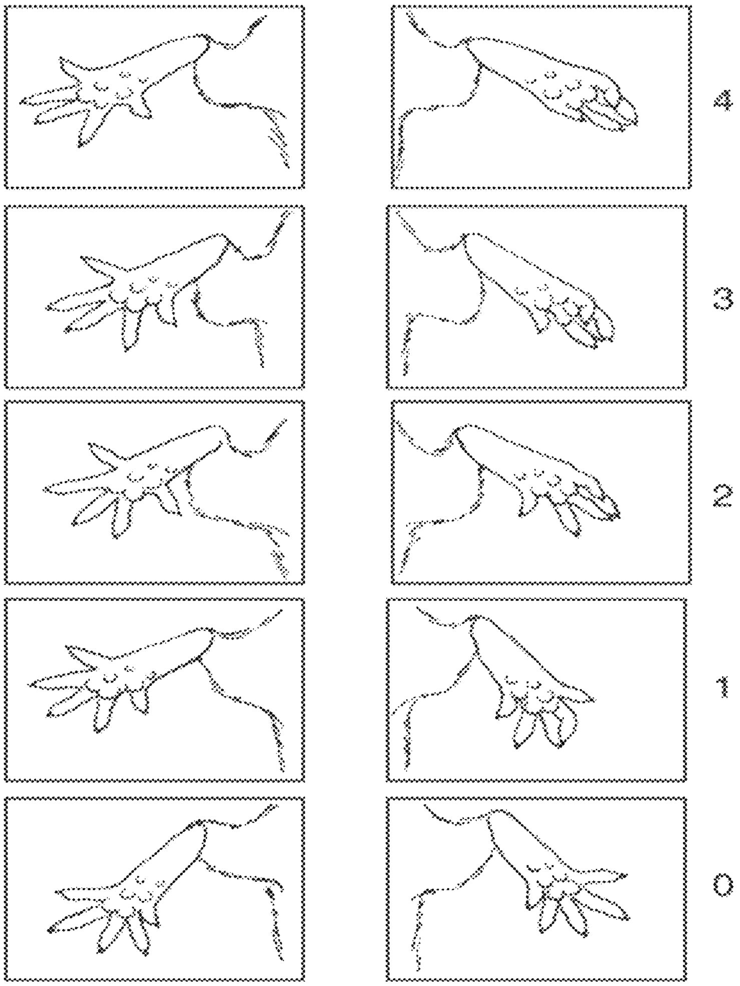
FIG. 9 presents a schematic illustration of the muscular paresis grading scale.

The activity of BTX was determined using single intramuscular (IM) administration of test items to mice (Hsd: ICRFemale), similar to the method disclosed in Aoki, K. R., "A Comparison of the Safety Margins of Botulinum Neurotoxin Serotypes A, B, and F in Mice", *Toxicol.* 2001, 39, 1815-1820, the contents of which are hereby incorporated by reference in their entirety. The effect of commercially available BTX-A solubilized in saline or gels, or released from gels by saline on the local muscle weakening was compared (saline injection served as negative control). Test animals were injected at a dose of about 20 U/kg body weight at a dose volume of 10 μl per animal to the right hind limb. A Digit Abduction Assay (DAS) was used to determine the local muscle weakening efficacy 48 hours after dosing. The DAS scoring was carried out by briefly suspending the animal by its tail to elicit a characteristic startle-response, namely causing the animal to extend its hind-limbs and abduct its respective hind digits. Reference is now made to FIG. 9, which depicts schematically the 5-point scale used to score the relative extent of BTX-A induced muscular paresis. According to this scale, a score of 0 represents a normal response, while a score of 4 represents the maximal reduction in digit abduction. The left column in FIG. 9 illustrates the scale for an untreated left hind leg, and the right column illustrates the scale for a treated right hind leg. The results are summarized in Table 1.

TABLE 1

Test results of BTX activity following intramuscular injection

| | Right hind leg (treated) | | Left hind leg (untreated) | |
|---|---|---|---|---|
| Group (n = 10) | Average score | SD | Average score | SD |
| Saline-control | 0 | 0 | 0 | 0 |
| BTX in saline | 2.5 | 0.97 | 0 | 0 |
| BTX in Gel A | 2.3 | 1.06 | 0 | 0 |
| BTX release from Gel A | 2.3 | 1.06 | 0 | 0 |
| BTX release from Gel A | 2.3 | 1.25 | 0 | 0 |
| BTX release from Gel A, pH adjusted to 5.2 | 3 | 1.05 | 0 | 0 |

The results demonstrate that the activity of BTX injected in Gel A or released from Gel A is similar to that of BTX in saline. A slight increase in the activity was observed for BTX release from Gel A that was pH adjusted (With HCl) to 5.2 (within the test SD). Low pH is known in the literature to promote BTX stability. Hence BTX administered to the bladder in Gel A (or similar gel formulations) is expected to preserve its biological activity within the gel and following its release from the gel. Moreover the gel is expected to increase BTX stability within the bladder by preserving its three dimensional structure and adjusting its surrounding conditions (as pH) in order to ensure its maximal stability during instillation.

Example 27

The enhanced effect of BTX following mixing with TheraCoat systems for treatment of bladder disorders was demonstrated in a bladder cystitis rat model. The testing method is described in Chuang, Y. C.; Yoshimura, N.; Huang, C. C.; Wua, M. "Intravesical Botulinum Toxin A Administration Inhibits COX-2 and EP4 Expression and Suppresses Bladder Hyperactivity in Cyclophosphamide-Induced Cystitis in Rats," *Eur. Urol.* 2008, 56, 159-167, which is hereby incorporated by reference in its entirety. Chronic cystitis was induced by intraperitoneal injection of cyclophosphamide (75 mg/kg was injected on day 1, 4 and 7). On day two, polyethylene tubing (PE-50) was inserted into the rat bladder through the urethra. The bladder was drained and instilled with gel or saline with and without BTX (1 ml, 20 u/ml Allergan). On day 8 the animal was anesthetized and the bladder was examined by data requisition POWER LAB via millar transducer inserted into the bladder dome. After recovery from anesthesia the animal was gently restrained and the suprapubic catheter was connected to infusion pump (0.08 ml/min continuously) and pressure transducer for recording of intravesical pressure and for saline infusion into the bladder in order to elicit repetitive voiding. The amplitude and the inter-contraction interval of reflex bladder contractions were recorded. Each treatment group comprised 2-4 animals.

Figure 2A:
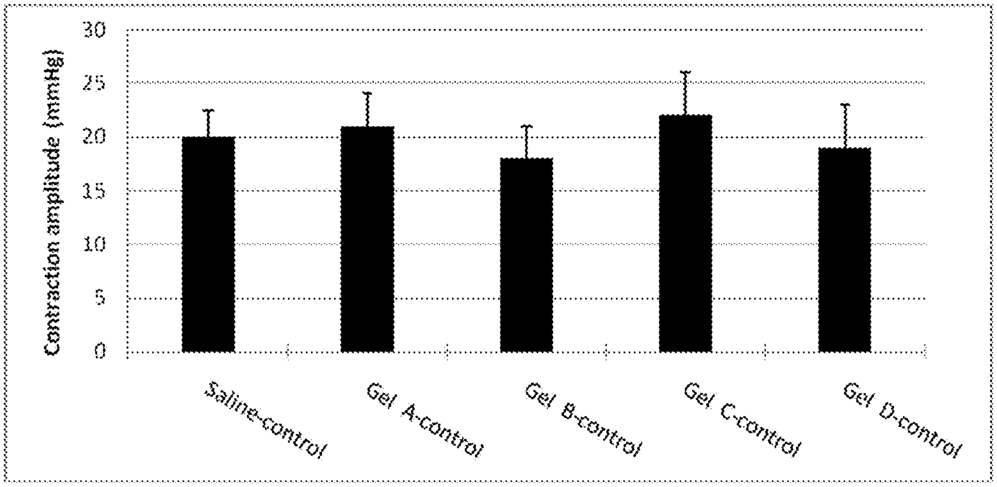
FIG. 2 presents graphs showing the amplitude (FIG. 2A) and inter-contraction interval (FIG. 2B) of bladder contractions in a control group of rats following treatment with saline or one of four thermoreversible hydrogel formulations.
Figure 2B:
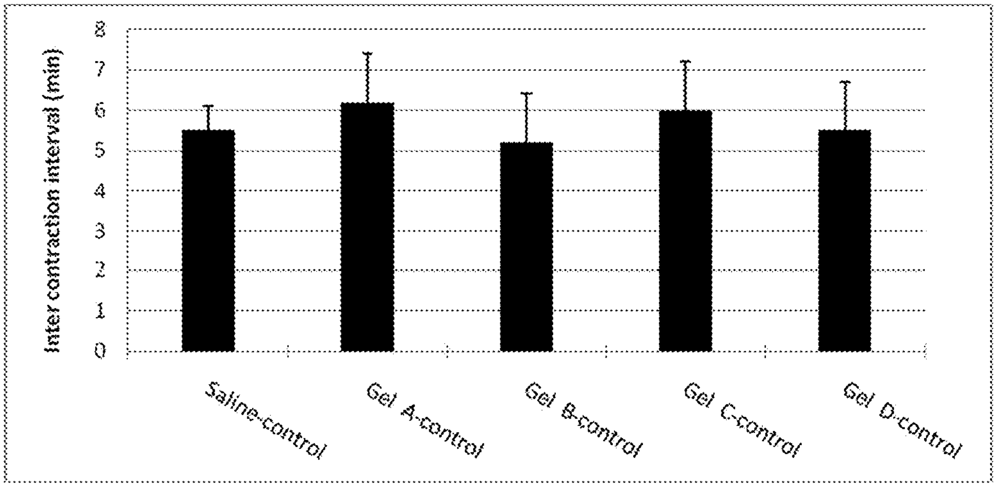
Figure 3A:
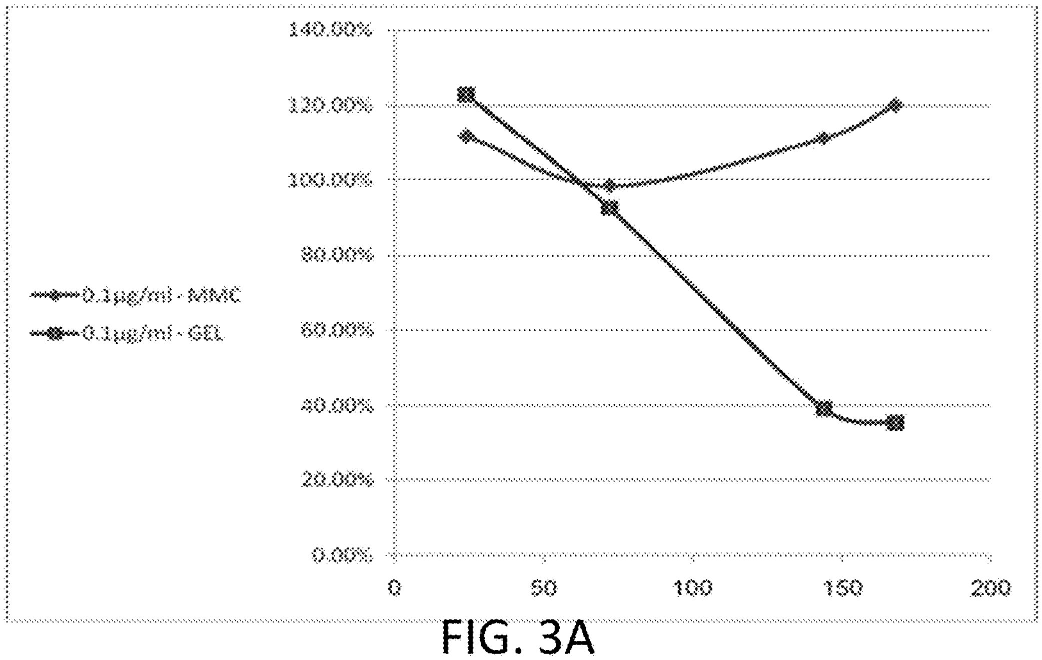
FIG. 3 presents graphs illustrating the MMC cytotoxicity when different MMC concentrations are used in saline (MMC) and in DTC-2 (GEL) respectively; MMC concentrations of 0.1 μg/ml (FIG. 3A); 0.5 μg/ml (FIG. 3B); 1 μg/ml (FIG. 3C); and 5 (FIG. 3D) μg/ml are shown.
Figure 3B:
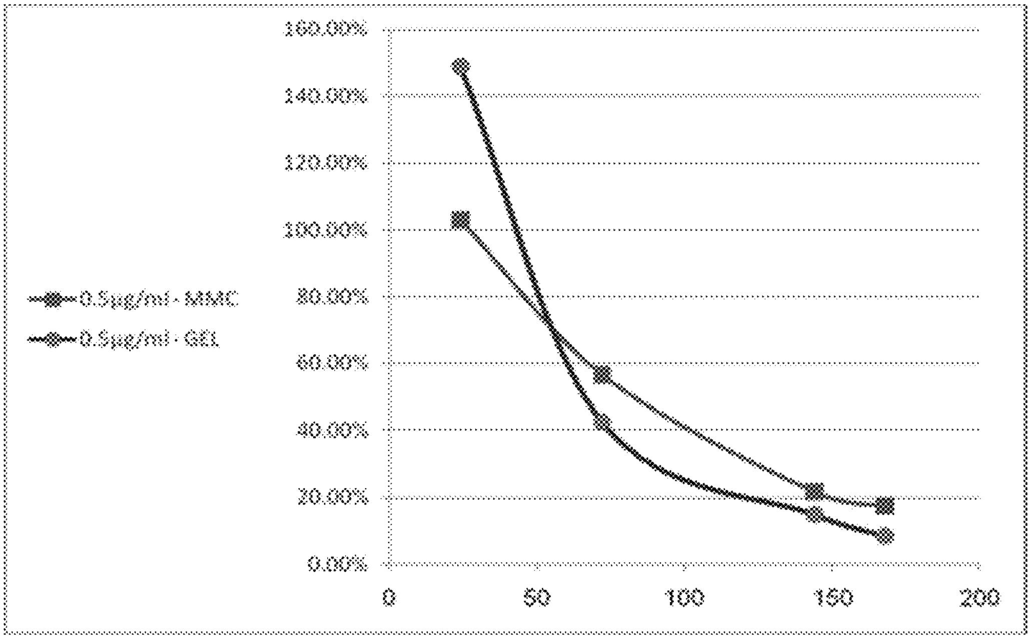
Figure 3C:
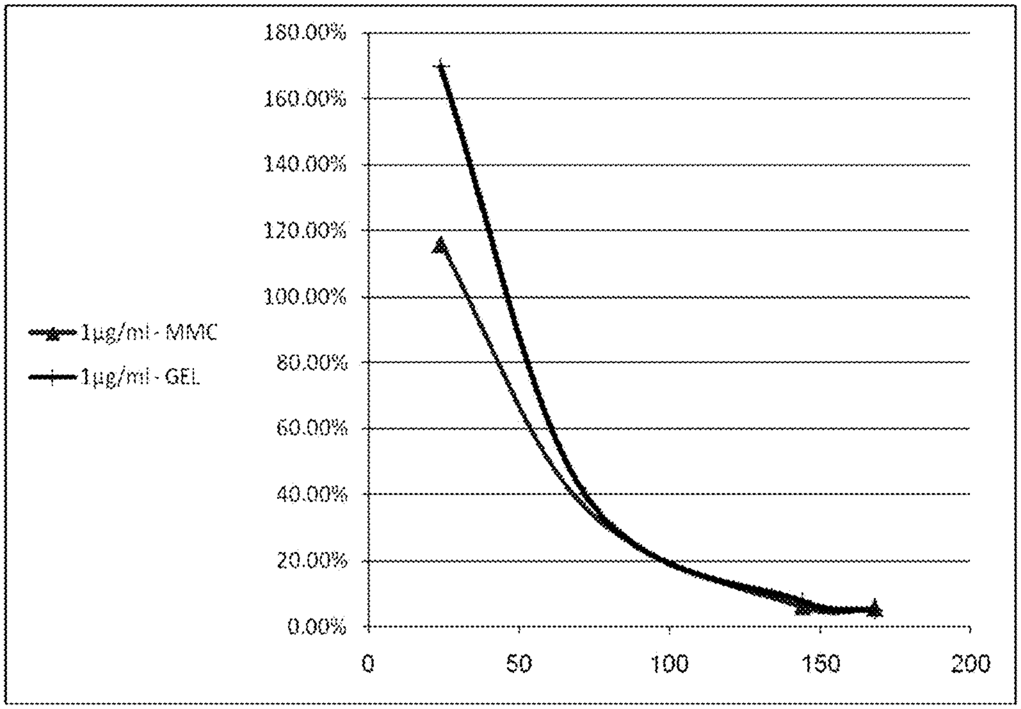
Figure 3D:
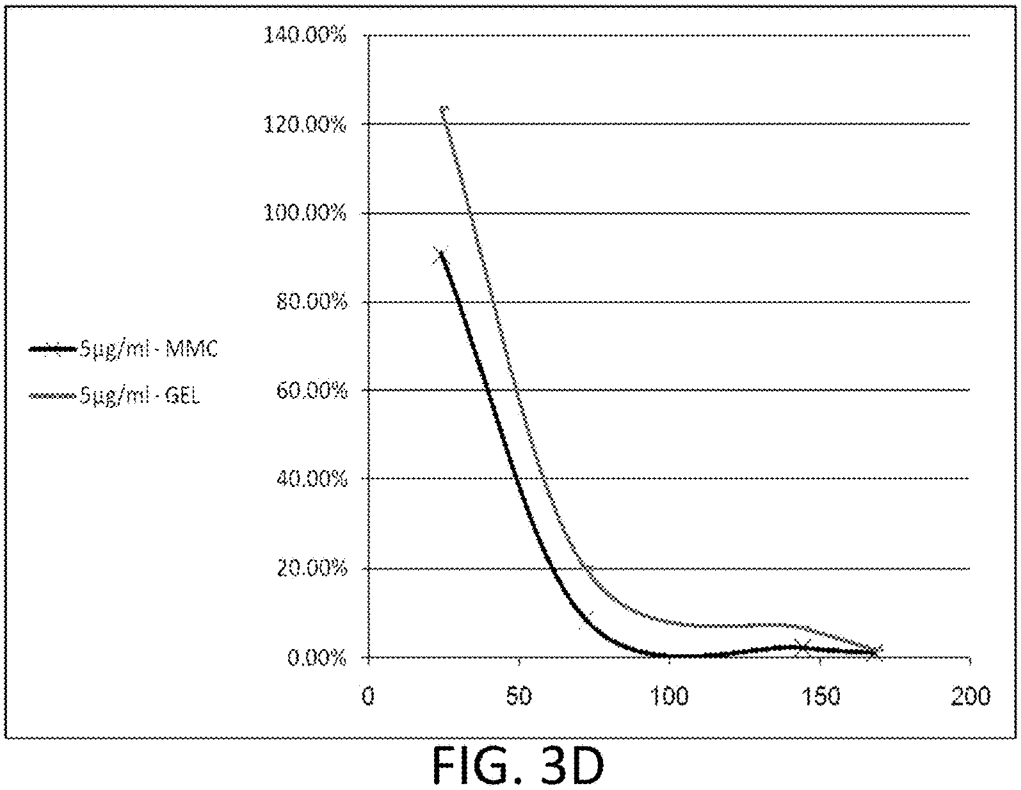
Figure 10A:
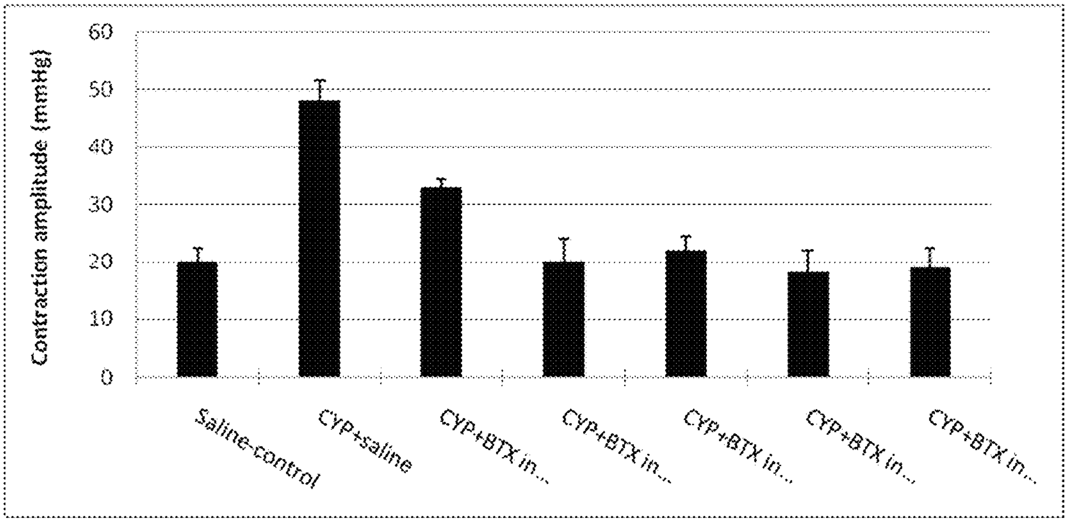
FIG. 10 presents graphs showing the contraction amplitude (FIG. 10A) and inter-contraction intervals (FIG. 10B) of bladder hyperactivity (chronic bladder cystitis) induced by intraperitoneal injection of cyclophosphamide in rats, showing suppression of bladder hyperactivity by treatment with botulinum toxin, and the improved suppression of bladder hyperactivity when the botulinum toxin is administered within a thermoreversible hydrogel according to several non-limiting embodiments of the invention disclosed herein.
Figure 10B:
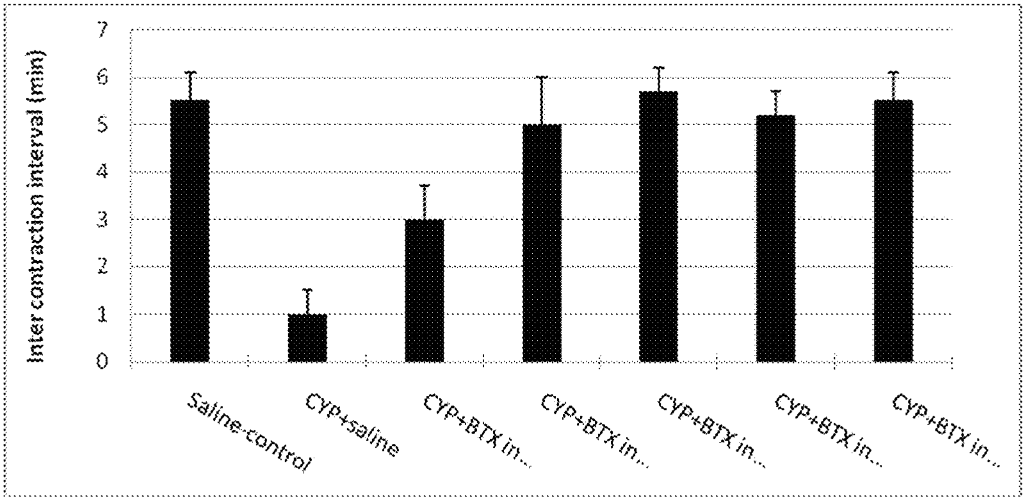

Reference is now made to FIG. 2, which presents graphs summarizing the amplitude (FIG. 2A) and inter-contraction interval (FIG. 2B) of rat bladder in control experiments in which the rats were treated with saline or a gel formulation not containing any therapeutic agent. Similar results were obtained for all treatments, suggestion that the gel formulations without BTX have no effect on the bladder. Reference is now made to FIG. 10, which presents graphs of contraction amplitude (FIG. 10A) and inter-contraction interval (FIG. 10B) following induction of bladder hyperactivity by intraperitoneal injection of cyclophosphamide (CYP). The bladder hyperactivity, as shown by a comparison of results for rats treated with CYP and saline to those for the control group treated by saline alone, is characterized by an increase in contraction amplitude and decrease in inter contraction interval. Rats that were administered with BTX reconstituted in saline or in gel formulations were shown to suppress the cyclophosphamide effect by decrease of contraction amplitude and increase of inter-contraction intervals. As shown in the figure, treatment by BTX incorporated into any one of the four gel formulations tested has a greater effect than treatment with BTX reconstituted in saline.

We claim:

1. A method for treating a patient with a bladder disorder characterized by bladder spasms, comprising:

preparing a pharmaceutical composition by incorporating into a biocompatible mucoadhesive thermoreversible hydrogel a therapeutically effective amount of at least one pharmaceutically active agent selected from the group of neurological blocking agents comprising botulinum toxin, botulinum toxin A, botulinum toxin B, botulinum toxin Cl, botulinum toxin D, botulinum toxin E, botulinum toxin F, botulinum toxin G;

and instilling said pharmaceutical composition into the urinary tract of the patient suffering from the bladder disorder;

wherein said instilling is at a temperature at which the pharmaceutical composition is liquid; whereby the pharmaceutical composition gels in contact with an internal wall of the urinary tract;

wherein the method does not comprise any step of injecting a pharmaceutically active agent into a wall of the bladder; and wherein the pharmaceutical composition has a viscosity of greater than 3000 Pa·s at 37° C.

2. The method according to claim 1, wherein the step of incorporating is performed up to two weeks prior to the step of applying.

3. The method according to claim 1, wherein the disorder is selected from the group consisting of urinary incontinence or urge due to unstable bladder or unstable detrusor sphincter; voiding complications; spinal cord injury; stroke or multiple sclerosis; bladder pathologies wherein a spasms are involved; interstitial cystitis; stress incontinence; urge incontinence; and neurogenic bladder.

4. The method according to claim 2, wherein the disorder is selected from the group consisting of urinary incontinence or urge due to unstable bladder or unstable detrusor sphincter; voiding complications; spinal cord injury; stroke or multiple sclerosis; bladder pathologies wherein a spasms are involved; interstitial cystitis; stress incontinence; urge incontinence; and neurogenic bladder.

5. The method according to claim 1, wherein the amount of the pharmaceutically active agent applied is about 0.2-20 U/kg body weight of botulinum toxin.

6. The method according to claim 1, wherein the pharmaceutical composition comprises at least one reverse thermal gelation agent and at least one component selected from the group consisting of mucoadhesive enhancers and thickening compounds.

7. The method according to claim 6, wherein the thermal reverse gelation agent comprises polymers and copolymers selected from the group consisting of: Chitosan, Polycarboxylic acids, polyglycolic acid polylactic acid and polyacrylic acid; polyurethanes; polyesters, poly(ethylene terephthalate); polyamides, nylon; polyacrylonitriles; polyphosphazenes; polylactones, polycaprolactone; polyanhydrides, poly[bis(pcarboxyphenoxy) propane anhydride; polyethylene; polyvinyl chloride; ethylene vinyl acetate; polyvinyl alcohol and polyvinyl acetate; Polylactide (PLA) and Poly(Lactide-co-Glycolide) (PLGA); Poloxamer block copolymers of the type polyethylene oxide-polypropylene-oxide, Poloxamer 407, Poloxamer 188, Poloxamer 338; cellulose polymers, hydroxypropylmethylcellulose (HPMC), hydroxyethylcellulose, and hydroxymethylcellulose.

8. The method according to claim 6, wherein the mucoadhesive enhancers and thickening compounds are selected from:

- the group consisting of polycarbophil, polyacrylic acids, crosslinked acrylic acid, polymethacrylates, divinyl glycol, vinylpyrrolidone/vinyl acetate copolymer, polyethylene glycol, cellulose, microcrystalline cellulose, gelatin, starch, gums, dicalcium phosphate, lactose, sucrose, PVP, PVA, PVAc, polysaccharides, waxes, fats, hyaluronic acid, k-carrageenan, carbomers, and Eudragitor;
- cellulose derivatives selected from the group consisting of methylcellulose, ethylcellulose, hydroxypropylmethylcellulose HPMC, methoxy-substituted HPMC with any possible degree of methoxy substitution (from 0 to 3), HPC, hydroxyalkylcelluloses, hydroxyalkylmethylcelluloses, L-HPC, HPMCAS, carboxymethylcelluloses, and salts thereof;
- starch derivatives selected from the group consisting of mono- and diphosphate ester starches;
- gums selected from the group consisting of gums selected from the group consisting of guar gum, locust beam gum, xanthan gum, and any combination thereof; and,
- polysaccharides selected from the group consisting of alginic acid, alginates, alginate esters, dextrin, cyclodextrin, and galactomannans.

9. The method according to claim 1, wherein the biocompatible mucoadhesive thermoreversible hydrogel is selected from the group consisting of:

i. ethylene oxide-propylene oxide triblock copolymer; at least one substance selected from the group consisting of CMC and HPMC; and the balance water;

ii. ethylene oxide-propylene oxide triblock copolymer; at least one substance selected from the group consisting of CMC and HPMC; polyethylene glycol; and the balance water;

iii. between 20% and 30% ethylene oxide-propylene oxide block copolymer; between 0.05% and 0.5% HPMC; between 0.1% and 2.5% PEG; and the balance water iv. between 20% and 30% ethylene oxide-propylene oxide block copolymer; between 0.1% and 0.3% HPMC; between 0.1% and 1.8% PEG; and the balance water;

v. 27% Poloxamer 407; 0.2% HPMC; 1% PEG; and the balance water;

vi. 20% Poloxamer 407; 0.2% sodium carboxymethylcellulose, 0.5% polyethylene glycol MW 20,000; citric acid-citrate buffer (50 mmol L-1 pH 5.2); and the balance water;

vii. between 20% and 30% Poloxamer 407; between 0.05% and 0.8% CMC; between 0.1% and 2.5% PEG; and the balance water;

viii. between 20% and 30% Poloxamer 407; between 10% and 20% Poloxamer 188;

between 0.05% and 2% CMC; between 0.1% and 2.5% PEG; and the balance water;

ix. 20% Poloxamer 407, 16% Poloxamer 188, 0.2%; sodium carboxymethylcellulose, 1% polyethylene glycol MW 3000, and the balance water;

x. between 20% and 30% Poloxamer 407; between 10% and 20% Poloxamer 188; between 0.05% and 0.8% k-carrageenan; between 0.1% and 2.5% PEG; and the balance water;

xi. 20% Poloxamer 407; 10% Poloxamer 188; 0.3% k-carrageenan; 1% PEG-400; and the balance water;

xii. between 18% and 30% (w/w) of an ethylene oxide/propylene oxide triblock copolymer, 0.05-10% PVP (polyvinylpyrrolidones), between 0% and 2.5% PEG-400, between 1-10% sodium caprylate, 1M-20 mM Tris HCl buffer and the balance water; and xiv. between 18% and 30% (w/w) of an ethylene oxide/propylene oxide triblock copolymer, 0.05-10% PVP (polyvinylpyrrolidones), between 0% and 2.5% PEG-400, 0.5-20% silica oxide 1M-20 mM Tris HCl buffer and the balance water; and xiv. 18% and 30% (w/w) of an ethylene oxide/propylene oxide triblock copolymer, 0.05-10% PVP (polyvinylpyrrolidones), between 0% and 2.5% PEG-400, 0.5-20% micronized cellulose 1M-20 mM Tris HCl buffer and the balance water.

10. A method for treating urinary incontinence, overacting bladder, interstitial cystitis, urge incontinence, and any bladder pathologies which involve bladder disorders, the method comprising administering to a subject in need of such treatment a pharmaceutical composition comprising a biocompatible mucoadhesive thermoreversible hydrogel and a therapeutically effective amount of an active agent comprising at least one neurological blocking agent selected from the group consisting of botulinum toxin of botulinum toxin A, botulinum toxin B, botulinum toxin Cl, botulinum toxin D, botulinum toxin E, botulinum toxin F, and botulinum toxin G;

wherein the step of administering comprises: instilling into the urinary tract of the subject the biocompatible mucoadhesive thermoreversible hydrogel at a temperature at which the pharmaceutical composition is liquid; whereby the pharmaceutical composition gels at body temperature in contact with an internal wall of urinary tract;

and wherein the mucoadhesive thermoreversible hydrogel composition has a viscosity of less than 200 Pa s at 10° C. and greater than 3000 Pa s at 37° C.

11. The method according to claim 1 or claim 10, wherein the biocompatible mucoadhesive thermoreversible hydrogel comprises between 20% and 30% ethylene oxide/propylene oxide triblock copolymer; between 0.05% and 0.5% HPMC; between 0.1% and 2.5% PEG; and the balance water.

12. The method according to claim 11, wherein the thermoreversible hydrogel comprises between 20% and 30% ethylene oxide/propylene oxide triblock copolymer; between 0.1% and 0.3% HPMC; between 0.1% and 1.8% PEG; and the balance water.

13. The method of claim 12, wherein the ethylene oxide/propylene oxide triblock copolymer is Poloxamer 407.

* * * * *